United States Patent [19]
Miyake et al.

[11] Patent Number: 5,614,654
[45] Date of Patent: Mar. 25, 1997

[54] ALUMINOSILOXANES, TITANOSILOXANES, (POLY)STANNOSILOXANES, AND THEIR PREPARATION

[75] Inventors: Masatoshi Miyake; Shunji Aoki, both of Usui-gun, Japan

[73] Assignee: Shin-Etsu Chemical Co., Ltd., Tokyo, Japan

[21] Appl. No.: 654,147

[22] Filed: May 28, 1996

[30] Foreign Application Priority Data

May 30, 1995 [JP] Japan ................................. 7-155139
May 30, 1995 [JP] Japan ................................. 7-155140
Jun. 27, 1995 [JP] Japan ................................. 7-183492

[51] Int. Cl.$^6$ ................................. C07F 7/08; C07F 7/22; C07F 7/28; C07F 5/06
[52] U.S. Cl. ................................. 556/10; 556/173
[58] Field of Search ................................. 556/10, 173

[56] References Cited

U.S. PATENT DOCUMENTS

| | | | |
|---|---|---|---|
| 3,657,149 | 4/1972 | Vandenberg | 556/173 X |
| 4,157,978 | 6/1979 | Llenado | 556/10 X |
| 4,298,543 | 11/1981 | Law et al. | 556/10 X |
| 4,400,327 | 8/1983 | Baskent et al. | 556/10 X |
| 5,391,529 | 2/1995 | Sangokoya | 556/173 X |

*Primary Examiner*—Paul F. Shaver
*Attorney, Agent, or Firm*—Millen, White, Zelano & Branigan, P.C.

[57] ABSTRACT

Novel aluminosiloxanes having an Al—O—Si linkage, titanosiloxanes having a Ti—O—Si linkage, and stannosiloxanes having a Sn—O—Si linkage in a molecule are provided. Aluminosiloxanes are formed by reacting aluminum alkoxides with cyclotrisiloxanes. Titanosiloxanes are formed by reacting titanium alkoxides with cyclotrisiloxanes. Stannosiloxanes are formed by reacting diorganotin dialkoxides with cyclotrisiloxanes. Reaction processes are simple.

18 Claims, 28 Drawing Sheets

ALUMINOSILOXANES, TITANOSILOXANES, (POLY)STANNOSILOXANES, AND THEIR PREPARATION

BACKGROUND OF THE INVENTION

1. Field of the Invention

This invention relates to novel aluminosiloxanes, titanosiloxanes, and (poly)stannosiloxanes and methods for preparing these siloxanes.

2. Prior Art

In the prior art, aluminosiloxanes and titanosiloxanes are generally prepared by effecting hydrolysis and condensation reaction of aluminum alkoxides and titanium alkoxides with alkoxysilanes. See Japanese Patent Application Kokai (JP-A) No. 123838/1988, "Inorganic Polymers I," Kajiwara & Murakami Ed., Sangyo Tosho K.K., "Polymer Complex 4, Organometallic Polymers," Polymer Complex Research Association Ed., Gakkai Shuppan Center K.K., and "Outlook on the Application of Inorganic Polymers," Kajiwara Ed., CMC K.K. To form Al—O—Si and Ti—O—Si linkages by these methods, unstable reactants such as condensable silicic acid and silanols and hydrolyzable alkoxysilanes must be used. The hydrolysis and condensation reaction has a drawback that the physical properties, molecular weight distribution, and Si/Al or Si/Ti molar ratio of products vary depending on reaction conditions including the amount of water added, the type and amount of catalyst used, the type of solvent, reaction temperature, and reaction time.

Most aluminosiloxanes and titanosiloxanes obtained by the above-mentioned methods have a wide molecular weight distribution. Depending on reaction conditions, there can be produced components free of an Al—O—Si or Ti—O—Si linkage in a molecule, that is, components whose backbone consists solely of Si—O—Si linkages. Such components are not useful in certain applications.

Further, aluminosiloxanes and titanosiloxanes obtained by the above-mentioned methods are stable only in solvents and when the solvents are removed, undergo gelation to convert into insoluble solids. Without solvents, they cannot be mixed with other ingredients to form compositions.

Stannosiloxanes known in the prior art include stannosiloxanes of formula (10), shown below, which are synthesized by effecting co-hydrolysis of tin chloride with chlorosilanes, reaction of alkyl metal silanolates with tin chloride, and reaction of distannoxane with silanols (see The Chemistry of Organotin Compounds, R. C. Poller, Logos Press Ltd., 1970), and stannosiloxanes of formula (11), shown below, which are synthesized through dealcoholysis reaction between tin alkoxides and silanols (see Y. Abe et al., Bull. Chem. Soc. Jpn., 45, 1258 (1972). To form Sn—O—Si linkages by these methods, unstable reactants such as condensable silanols and hydrolyzable chlorosilanes must be used.

$$R'_3SiOSnR''_3 \quad (10)$$

In formula (10), each of R' and R" is an alkyl or aryl group.

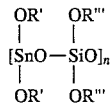
(11)

In formula (11), R' is a tert-butyl group and R'" is a tri-tert-butoxysilyl group.

It is also known from A. Kasgoz et al., J. Ceramic Soc. Jpn., 100, 763 (1992) that dehydrochlorination reaction between tin chloride and silicic acid yields a stannosiloxane of the following formula (12).

However, this method has a drawback that the physical properties, molecular weight distribution, and Sn/Si molar ratio of products vary depending on reaction conditions including the type of solvent, reaction temperature, and reaction time. Further, polystannosiloxanes obtained by this method remain stable only in solvents and when the solvents are removed, undergo gelation to convert into insoluble solids. Without solvents, they cannot be mixed with other ingredients to form compositions.

SUMMARY OF THE INVENTION

An object of the invention is to provide a novel aluminosiloxane, titanosiloxane and (poly)stannosiloxane which have overcome the above-mentioned problems and a method for preparing the same.

We have found that a novel aluminosiloxane or titanosiloxane of formula (1) or (4) having at least one Al—O—Si or Ti—O—Si linkage in its molecule can be prepared by reacting an aluminum alkoxide of formula (2) or titanium alkoxide of formula (5) with a cyclotrisiloxane of formula (3) as shown below.

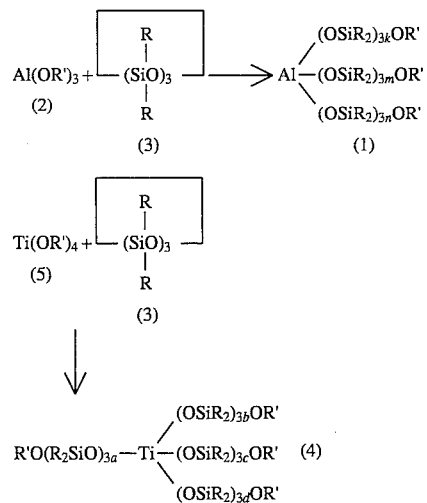

In the formulae, R is a hydrogen atom or a substituted or unsubstituted monovalent hydrocarbon group having 1 to 20 carbon atoms, R' is a substituted or unsubstituted monovalent hydrocarbon group having 1 to 10 carbon atoms, letters k, m, n, a, b, c, and d are positive integers inclusive of 0, and $k+m+n \geq 1$ and $a+b+c+d \geq 1$.

The reaction shown by the above scheme can start with cyclic siloxanes which are easy to handle. The molar ratio of Si/Al or Si/Ti can be easily controlled because it is determined by the molar ratio of cyclic siloxane to aluminum alkoxide or titanium alkoxide as charged. A component free of an Al—O—Si or Ti—O—Si linkage in a molecule is unlikely to form. Since neither hydrolysis nor condensation reaction is needed to form an Al—O—Si or Ti—O—Si linkage, the physical properties, molecular weight distribution, and Si/Al or Si/Ti molar ratio of products do not vary depending on reaction conditions. Thus aluminosiloxanes and titanosiloxanes can be produced in a commercially advantageous manner. The resultant aluminosiloxanes and titanosiloxanes remain as flowing liquids even after removal of solvents and can be readily mixed with other ingredients. Because of the inclusion of a trisiloxane unit in a molecule, they are well compatible with other silicone resins. Because of the inclusion of three or four alkoxy groups in a molecule, they can be formulated into curable compositions which take advantage of the alkoxy groups. The aluminosiloxanes of formula (1) or titanosiloxanes of formula (4) not only form cured products when used alone or as a main component, but are also useful as a catalyst for the polymerization and curing of monomers and resins which are curable with aluminum or titanium system Lewis acid catalysts (e.g., monomers and oligomers containing epoxide, vinyl ether or cyclic ether).

We have also found that a novel stannosiloxane of formula (6) can be prepared by reacting a tin compound of formula (8) with a cyclotrisiloxane of formula (9) as shown below and that a polystannosiloxane of formula (7) can be prepared by subjecting the stannosiloxane to hydrolysis and polycondensation as shown below.

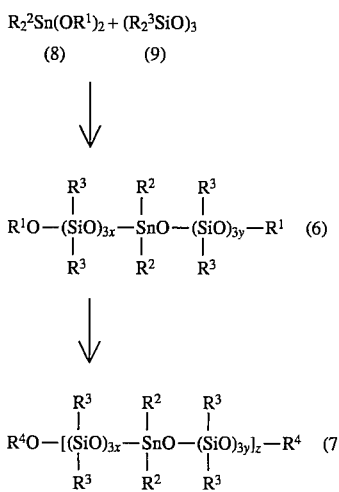

In the formulae, $R^1$ and $R^2$ are independently selected from substituted or unsubstituted monovalent hydrocarbon groups having 1 to 20 carbon atoms, $R^3$ is independently a hydrogen atom or substituted or unsubstituted monovalent hydrocarbon group having 1 to 10 carbon atoms, $R^4$ is a hydrogen atom or a group as defined for $R^1$, letters x and y are 0 or positive integers of at least 1 with the proviso that both x and y are not equal to 0 at the same time, and z is an integer of at least 2.

The method ensures the preparation of (poly)stannosiloxanes of formulae (6) and (7) in a simple manner using cyclic siloxanes which are easy to handle. Since the molar ratio of Sn/Si is determined by the molar ratio of diorganotin dialkoxide to cyclotrisiloxane as charged and neither hydrolysis nor condensation reaction nor catalyst is needed to form an Sn—O—Si linkage, the physical properties, molecular weight distribution, and Sn/Si molar ratio of products do not vary depending on reaction conditions. A component free of an Sn—O—Si linkage in a molecule is unlikely to form. The resultant stannosiloxanes remain as smoothly flowing liquids even after removal of solvents and can be readily mixed with other ingredients. Because of the inclusion of a trisiloxane unit in a molecule, they are well compatible with other silicone resins. Because of the inclusion of two alkoxy groups in a molecule, they can be formulated into curable compositions which take advantage of the alkoxy groups. The (poly)stannosiloxanes of the invention not only form cured products when used as a main component, but are also useful as a catalyst for the polymerization and curing of monomers and resins which are curable with tin-containing Lewis acid catalysts.

Accordingly, in a first aspect, the present invention provides an aluminosiloxane of formula (1) and a method for preparing an aluminosiloxane of formula (1) by reacting an aluminum alkoxide of formula (2) with a cyclotrisiloxane of formula (3).

In a second aspect, the present invention provides a titanosiloxane of formula (4) and a method for preparing a titanosiloxane of formula (4) by reacting a titanium alkoxide of formula (5) with a cyclotrisiloxane of formula (3).

In a third aspect, the present invention provides a stannosiloxane of formula (6), a polystannosiloxane of formula (7), a method for preparing a stannosiloxane of formula (6) by reacting a tin compound of formula (8) with a cyclotrisiloxane of formula (9), and a method for preparing a polystannosiloxane of formula (7) by subjecting a stannosiloxane of formula (6) to hydrolysis and polycondensation.

BRIEF DESCRIPTION OF THE DRAWINGS

These and further features of the present invention will be apparent with reference to the following description and drawings, wherein.

DETAILED DESCRIPTION OF THE INVENTION

Aluminosiloxane

Figure 1:
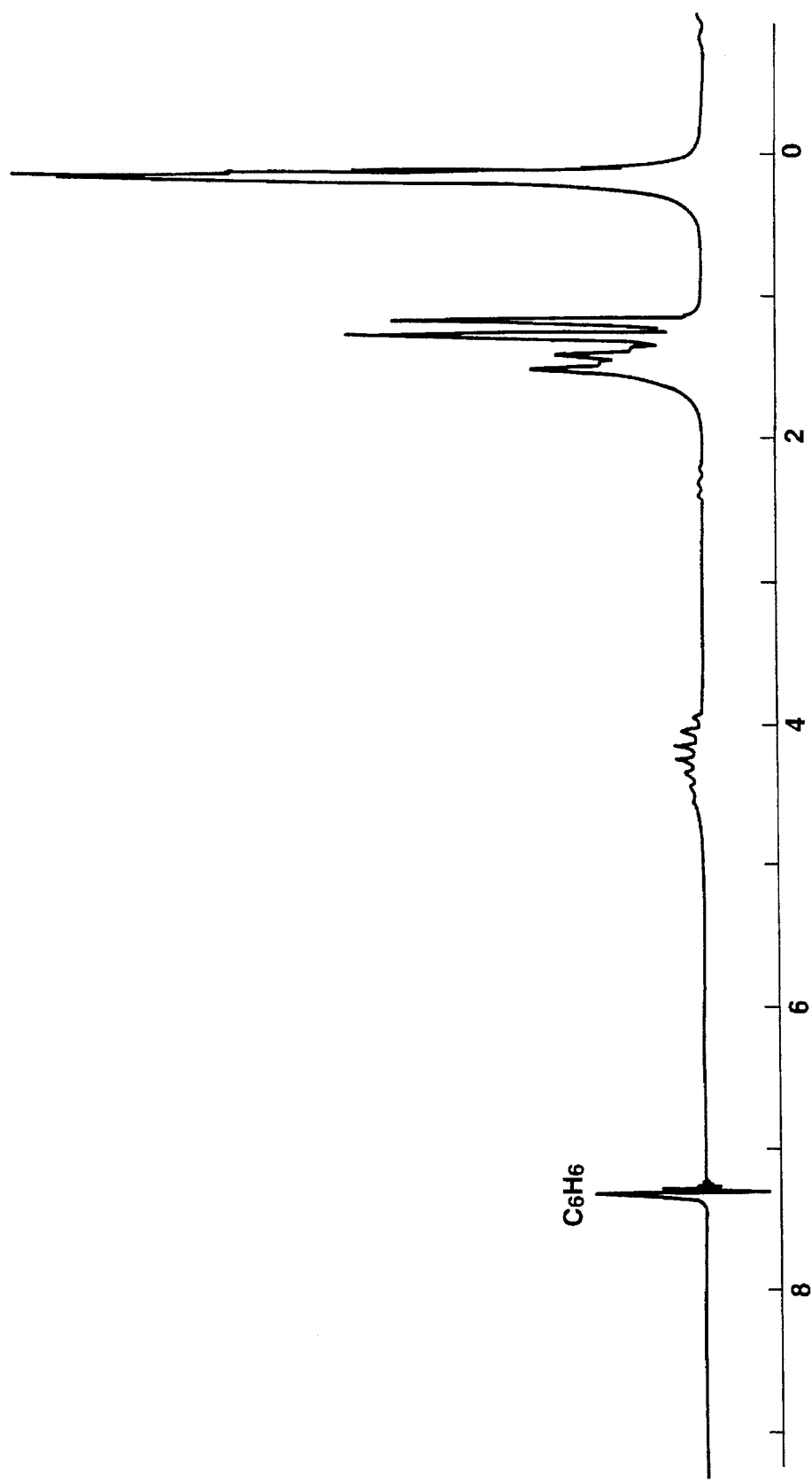
FIG. 1 is a $^1$H-NMR spectrum of the product of Example 1.

In the first aspect, the invention provides a novel aluminosiloxane of the following general formula (1).

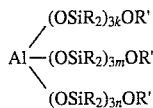

(1)

R is a hydrogen atom or a substituted or unsubstituted monovalent hydrocarbon group having 1 to 20 carbon atoms. The R groups may be identical or different. Examples of the monovalent hydrocarbon group include alkyl groups such as methyl, ethyl, propyl and butyl; cycloalkyl groups such as cyclohexyl; aryl groups such as phenyl and tolyl; alkenyl groups such as vinyl, allyl, and hexenyl; and substituted ones of these groups wherein some or all of the hydrogen atoms attached to carbon atoms are replaced by cyano groups, alkoxy groups, halogen atoms or the like, such as cyanoethyl, 2-methoxyethyl, 3-chloropropyl, and 3,3,3-trifluoropropyl groups.

R' is a substituted or unsubstituted monovalent hydrocarbon group having 1 to 10 carbon atoms, for example, alkyl, alkenyl and aryl groups as exemplified above. Alkyl groups of 1 to 5 carbon atoms are preferred.

Letters k, m, and n are positive integers inclusive of 0, preferably 0 to 5, especially 0 to 3, and the sum of k+m+n is at least 1, preferably 1 to 15, especially 1 to 9.

Examples of the aluminosiloxane of formula (1) are shown below using an average compositional formula. In the formulae, iPr is isopropyl, Me is methyl, and Bu is butyl.

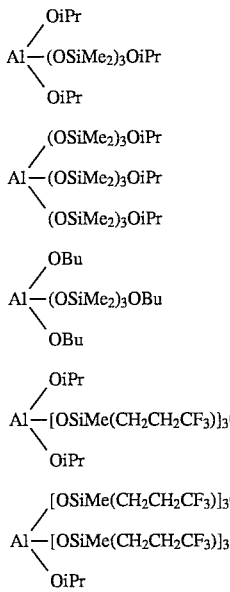

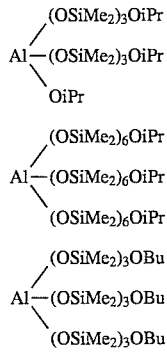

The aluminosiloxane of formula (1) can be prepared by reacting an aluminum alkoxide of the following general formula (2):

$$Al(OR')_3 \quad (2)$$

with a cyclotrisiloxane of the following general formula (3):

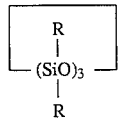

(3)

In the formulae, R and R' are as defined above. Examples of the aluminum alkoxide of formula (2) include aluminum (III) triethoxide, aluminum (III) triisopropoxide, aluminum (III) tri-n-butoxide, aluminum (III) tri-s-butoxide, and aluminum (III) tri-t-butoxide. Examples of the cyclotrisiloxane of formula (3) include hexamethylcyclotrisiloxane, hexaethylcyclotrisiloxane, hexaphenylcyclotrisiloxane, 1,3,5-triphenyl-1,3,5-trimethylcyclotrisiloxane, 1,3,5-trivinyl-1,3,5-trimethylcyclotrisiloxane, 1,3,5-tri(3,3,3-trifluoropropyl)-1,3,5-trimethylcyclotrisiloxane, 1-phenyl-1,3,3,5,5-pentamethylcyclotrisiloxane, 1,1-diphenyl-3,3,5,5-tetramethylcyclotrisiloxane, and 1-(3,3,3-trifluoropropyl)-1,3,3,5,5-pentamethylcyclotrisiloxane.

In the practice of the invention, reaction between aluminum alkoxide and cyclotrisiloxane may be carried out by adding an aluminum alkoxide or a mixture of aluminum alkoxides to a cyclotrisiloxane or a mixture of cyclotrisiloxanes or vice versa in an inert gas atmosphere such as dry nitrogen and dry argon, and allowing reaction to take place at room temperature to about 300° C., preferably room temperature to about 150° C. The reaction time is not critical although it is generally about ½ to 72 hours. An organic solvent is used if desired. Exemplary organic solvents include hydrocarbon solvents such as hexane, octane, toluene and xylene, alcohols such as isopropanol and butanol, esters such as butyl acetate and ethyl acetate, ether solvents such as diethyl ether, diisopropyl ether, dibutyl ether, and dioxane, and ketone solvents such as acetone, methyl ethyl ketone, methyl isobutyl ketone, and cyclohexanone.

The ratio of aluminum alkoxide and cyclotrisiloxane charges is not critical. The charge ratio is generally such that the molar ratio of Si/Al may range from 3/1 to 99/1 although a molar ratio Si/Al ranging from 3/1 to 45/1 is preferred for preventing formation of a component which is free of an aluminosiloxane (Al—O—Si) linkage in a molecule.

The aluminosiloxane of the invention is recovered from the reaction product by removing the volatiles therefrom at elevated temperature and/or in vacuum, if necessary.

Titanosiloxane

In the second aspect, the invention provides a novel titanosiloxane of the following general formula (4).

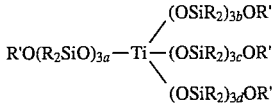

(4)

In formula (4), R and R' are as defined for formula (1), letters a, b, c, and d are positive integers inclusive of 0, preferably 0 to 5, especially 0 to 3, and the sum of a+b+c+d is at least 1, preferably 1 to 20, especially 1 to 12.

Examples of the titanosiloxane of formula (4) are shown below using an average compositional formula. In the formulae, iPr is isopropyl, Me is methyl, and Bu is butyl.

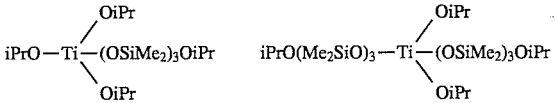

-continued

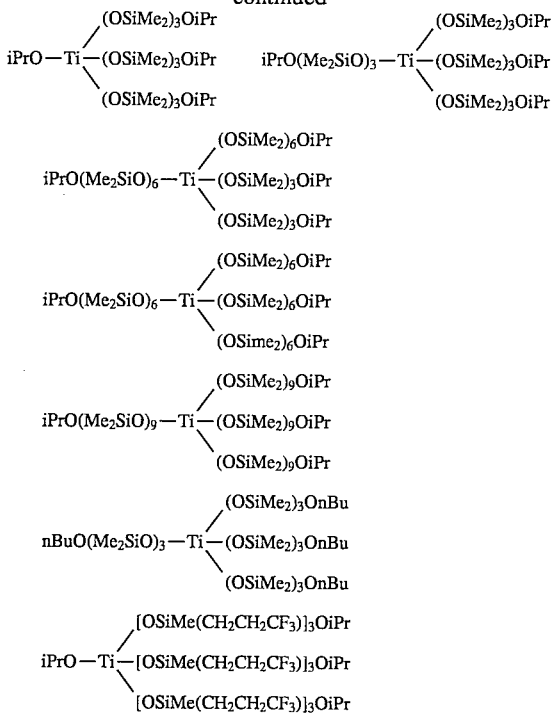

The titanosiloxane of formula (4) can be prepared by reacting a titanium alkoxide of the following general formula (5):

$$Ti(OR')_4 \quad (5)$$

with a cyclotrisiloxane of the following general formula (3):

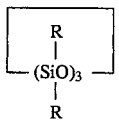

In the formulae, R and R' are as defined above. Examples of the titanium alkoxide of formula (5) include titanium (IV) tetramethoxide, titanium (IV) tetraethoxide, titanium (IV) tetraisopropoxide, titanium (IV) tetra-n-butoxide, titanium (IV) tetra-s-butoxide, and titanium (IV) tetra-t-butoxide. Examples of the cyclotrisiloxane of formula (3) are as described above.

In the practice of the invention, reaction between titanium alkoxide and cyclotrisiloxane may be carried out by adding a titanium alkoxide or a mixture of titanium alkoxides to a cyclotrisiloxane or a mixture of cyclotrisiloxanes or vice versa in an inert gas atmosphere such as dry nitrogen and dry argon, and allowing reaction to take place at room temperature to about 300° C., preferably room temperature to about 150° C. The reaction time is not critical although it is generally about ½ to 72 hours. An organic solvent is used if desired. Exemplary organic solvents include hydrocarbon solvents such as hexane, octane, toluene and xylene, alcohols such as isopropanol and butanol, esters such as butyl acetate and ethyl acetate, ether solvents such as diethyl ether, diisopropyl ether, dibutyl ether, and dioxane, and ketone solvents such as acetone, methyl ethyl ketone, methyl isobutyl ketone, and cyclohexanone.

The ratio of titanium alkoxide and cyclotrisiloxane charges is not critical. The charge ratio is generally such that the molar ratio of Si/Ti may range from 3/1 to 99/1 although a molar ratio Si/Ti ranging from 3/1 to 60/1 is preferred for preventing formation of a component which is free of a titanosiloxane (Ti—O—Si) linkage in a molecule.

The titanosiloxane of the invention is recovered from the reaction product by removing the volatiles therefrom at elevated temperature and/or in vacuum, if necessary.

The aluminosiloxanes of formula (1) and titanosiloxanes of formula (4) are especially useful in the following applications.

(1) heat resistant, mar resistant coatings, sealants, adhesives, and tackifiers (2) curing catalysts for condensation curable silicone resins (3) curing catalysts for epoxy monomers, epoxy resins, vinyl ether monomers and oligomers, cyclic ether monomers and oligomers (4) additives to condensation curable silicone resins for increasing the refractive index and hardness of cured coatings or imparting electric conductivity, antistatic property, and mar resistance to cured coatings (5) precursors of ceramic and glass sintered bodies (6) precursors of olefin polymerizing catalysts (7) coupling agents and primers (8) plasticizers for vinyl chloride resins Since each of the aluminosiloxanes and titanosiloxanes of the invention has at least one trisiloxane unit and three or four alkoxy groups in a molecule, it is a smoothly flowing liquid, is well miscible with other ingredients, especially well soluble in various silicone resins, and has curability. Because of these properties, it finds use in the above-mentioned applications. The method of the invention ensures the preparation of aluminosiloxanes and titanosiloxanes in a simple manner using cyclic siloxanes which are easy to handle.

Stannosiloxane

In the third aspect, the invention provides a novel stannosiloxane and polystannosiloxane having an Sn—O—Si linkage and a trisiloxane unit in a molecule. They are represented by the following general formulae (6) and (7).

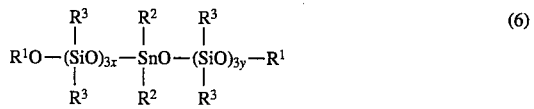

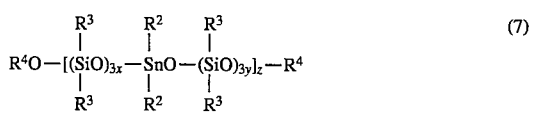

In the formulae, each of $R^1$ and $R^2$, which may be the same or different, is selected from substituted or unsubstituted monovalent hydrocarbon groups having 1 to 20 carbon atoms, for example, alkyl groups such as methyl, ethyl, propyl and butyl; cycloalkyl groups such as cyclohexyl; alkenyl groups such as vinyl, allyl, and hexenyl; aryl groups such as phenyl and tolyl; and substituted ones of these groups wherein some or all of the hydrogen atoms attached to carbon atoms are replaced by cyano groups, halogen atoms or the like, such as cyanoethyl, 3-chloropropyl, and 3,3,3-trifluoropropyl groups. Alkyl groups of 1 to 10 carbon atoms are preferred.

$R^4$ is a hydrogen atom or a group similar to $R^1$.

$R^3$ is a hydrogen atom or a substituted or unsubstituted monovalent hydrocarbon group having 1 to 10 carbon atoms, for example, alkyl groups such as methyl, ethyl, propyl and butyl; cycloalkyl groups such as cyclohexyl; aryl groups such as phenyl and tolyl; alkenyl groups such as vinyl, allyl, and hexenyl; and substituted ones of these groups wherein some or all of the hydrogen atoms attached to carbon atoms are replaced by cyano groups, alkoxy groups, halogen atoms or the like, such as cyanoethyl, 2-methoxyethyl, 3-chloropropyl, and 3,3,3-trifluoropropyl groups. It is noted that the two $R^3$ groups attached to a common Si atom may be the same or different.

Letters x and y are 0 or integers of at least 1 with the proviso that both x and y are not equal to 0 at the same time. It is preferred that $1 \leq x+y \leq 33$. Letter z is an integer of at least 2. The upper limit of z varies depending on a degree of condensation resulting from hydrolysis and polycondensation to be described later although it is preferred that $z \leq 1,000$, especially $z \leq 100$.

Examples of the stannosiloxane of formula (6) are shown below using an average compositional formula. In the formulae, Me is methyl, Bu is butyl, and Oc is octyl.

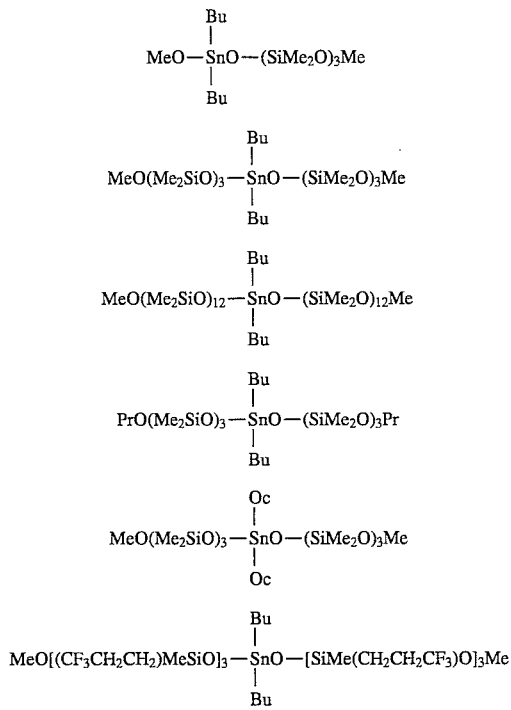

On hydrolysis and polycondensation of the stannosiloxane, there is obtained a polystannosiloxane of formula (7). Its examples are shown by the following average compositional formulae.

HO-[(Bu$_2$SnO)$_1$-(Me$_2$SiO)$_6$]$_z$-H

HO-[(Bu$_2$SnO)$_1$-(Me$_2$SiO)$_{24}$]$_z$-H

HO-[(Bu$_2$SnO)$_1$-((CF$_3$CH$_2$CH$_2$)MeSiO)$_6$]$_z$-H

The stannosiloxane of formula (6) can be prepared by reacting a diorganotin dialkoxide of the following general formula (8):

$$R^2{}_2Sn(OR^1)_2 \qquad (8)$$

wherein $R^1$ and $R^2$ are as defined above with a cyclotrisiloxane of the following general formula (9):

$$(R^3{}_2SiO)_3 \qquad (9)$$

wherein $R^3$ is as defined above.

Examples of the diorganotin dialkoxide of formula (8) include dibutyltin dimethoxide, dioctyltin dimethoxide, and dibutyltin dipropoxide. Examples of the cyclotrisiloxane of formula (9) are as described in conjunction with formula (3).

In preparing the stannosiloxane of formula (6), reaction of a diorganotin dialkoxide of formula (8) with a cyclotrisiloxane of formula (9) is carried out as follows.

For example, reaction may be carried out by adding a diorganotin dialkoxide or a mixture of diorganotin dialkoxides to a cyclotrisiloxane or a mixture of cyclotrisiloxanes or vice versa in an inert gas atmosphere such as dry nitrogen and dry argon, and allowing reaction to take place at room temperature to about 300° C., preferably room temperature to about 150° C. An organic solvent is used if desired. Exemplary organic solvents include hydrocarbon solvents such as hexane, octane, toluene and xylene, alcohols such as isopropanol and butanol, esters such as butyl acetate and ethyl acetate, ether solvents such as diethyl ether, diisopropyl ether, dibutyl ether, and dioxane, and ketone solvents such as acetone, methyl ethyl ketone, methyl isobutyl ketone, and cyclohexanone.

The ratio of diorganotin dialkoxide and cyclotrisiloxane charges is not critical. The charge ratio is generally such that the molar ratio of Sn/Si may range from 1/999 to 1/3 although a molar ratio Sn/Si ranging from 1/99 to 1/3 is preferred for preventing formation of a component which is free of a stannosiloxane (Sn—O—Si) linkage in a molecule.

The above-mentioned reaction yields a stannosiloxane of formula (6). If desired, a polystannosiloxane of formula (7) can be obtained by subjecting some or all of hydrolyzable groups at molecular ends of the stannosiloxane to hydrolysis and polycondensation. This may be accomplished by adding water or a mixture of water and an organic solvent to the reaction mixture and effecting hydrolysis reaction at room temperature to about 200° C. to form a condensation product.

In either case, there is obtained a reaction product containing a (poly)stannosiloxane. The (poly)stannosiloxane of the invention is recovered from the reaction product by removing the volatiles therefrom at elevated temperature and/or in vacuum, if necessary.

The (poly)stannosiloxanes of the invention are especially useful in the following applications, for example.

(1) curing catalysts for condensation curable silicone resins (2) heat resistant, mar resistant coatings, sealants, adhesives, and tackifiers (3) additives to condensation curable silicone resins for increasing the refractive index and hardness of cured coatings or imparting electric conductivity, antistatic property, and mar resistance to cured coatings (4) curing catalysts for epoxy monomers, epoxy resins, vinyl ether monomers and oligomers, cyclic ether monomers and oligomers (5) plasticizers for vinyl chloride resins (6) precursors of ceramic and glass sintered bodies (7) precursors of olefin polymerizing catalysts The method of the invention ensures the preparation of (poly)stannosiloxanes of formulae (6) and (7) in a simple manner using cyclic siloxanes which are easy to handle. Since the molar ratio of Sn/Si is determined by the molar ratio of diorganotin dialkoxide to cyclotrisiloxane as charged and neither hydrolysis nor condensation reaction nor catalyst is needed to form an Sn—O—Si linkage, the physical properties, molecular weight distribution, and Sn/Si molar ratio of products do not vary depending on reaction conditions. A component free of an Sn—O—Si linkage in a molecule is unlikely to form. The resultant stannosiloxanes remain as smoothly flowing liquids even after removal of solvents and can be readily mixed with other ingredients. Because of the inclusion of a trisiloxane unit in a molecule, they are well compatible with other silicone resins. Because of the inclusion of two alkoxy groups in a molecule, they can be formulated into curable compositions which take advantage of the alkoxy groups. The (poly)stannosiloxanes of the invention not only form cured products when used as a main component, but are also useful as a catalyst for the polymerization and curing of monomers and resins which are curable with tin-containing Lewis acid catalysts (e.g., monomers and oligomers containing epoxide, vinyl ether or cyclic ether). The (poly)stannosiloxanes of the invention are well soluble in various silicone resins and useful as a curing catalyst.

EXAMPLE

Examples of the invention are given below by way of illustration and not by way of limitation. Note that iPr is isopropyl, Me is methyl, Bu is butyl, and nBu is normal butyl.

Example 1

Figure 2:
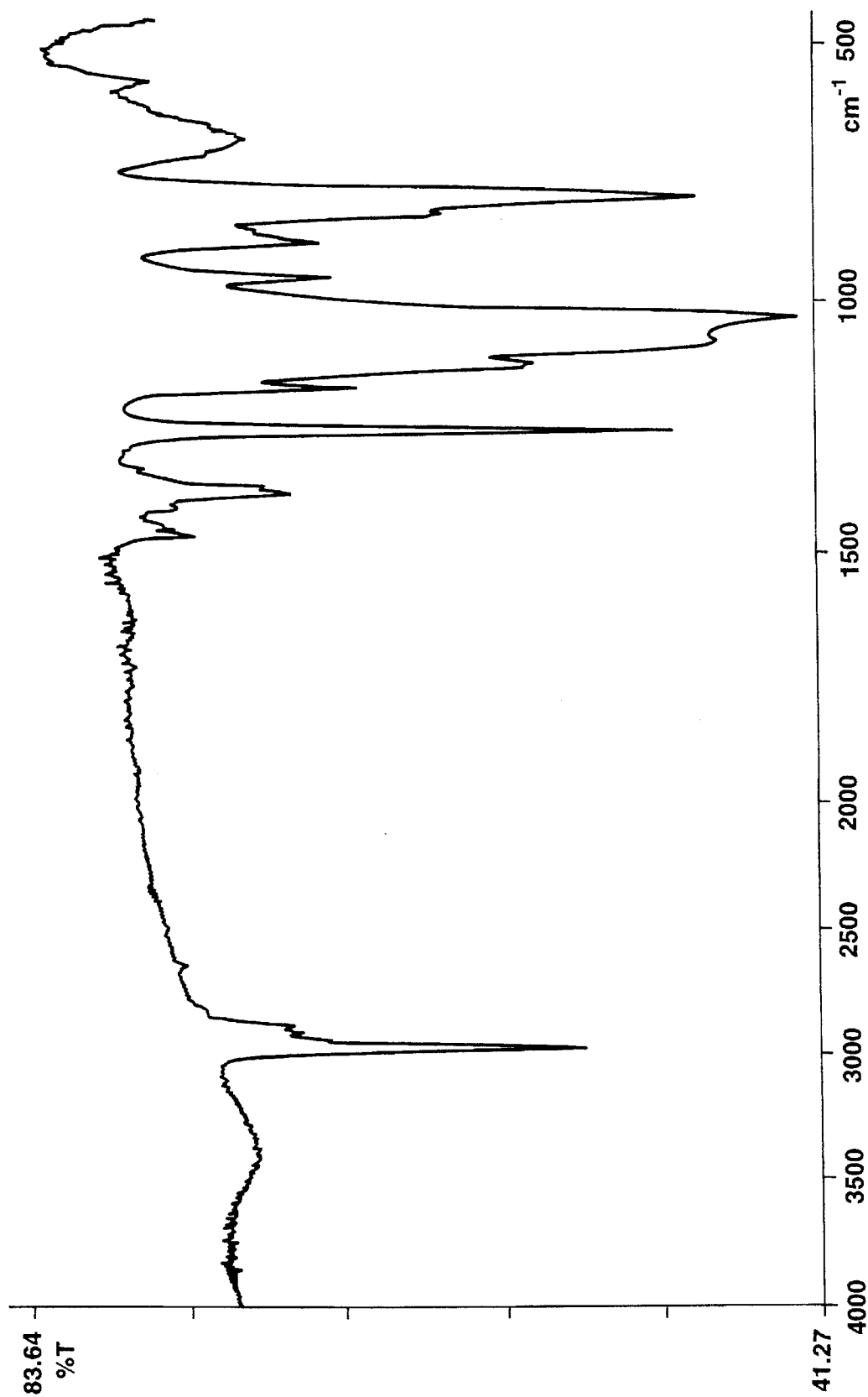
FIG. 2 is an IR spectrum of the product of Example 1.

A 300-ml four-necked flask equipped with a stirrer, condenser, thermometer, and dropping funnel was charged with 66.6 grams of hexamethylcyclotrisiloxane and 61.4 grams of aluminum (III) triisopropoxide. In a nitrogen atmosphere, the contents were heated and stirred at 140° C. for 10 hours. After the disappearance of hexamethylcyclotrisiloxane was acknowledged by gas chromatography, the flask was cooled to room temperature. The volatiles were distilled off at 120° C. and 4 mmHg. The product (105 grams) was a clear liquid. On analysis of $^1$H-NMR spectrum (FIG. 1) and IR spectrum (FIG. 2), it was identified to be an aluminosiloxane having an Si—O—Al linkage in a molecule represented by the following average compositional formula.

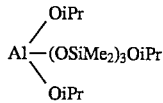

Example 2

Figure 3:
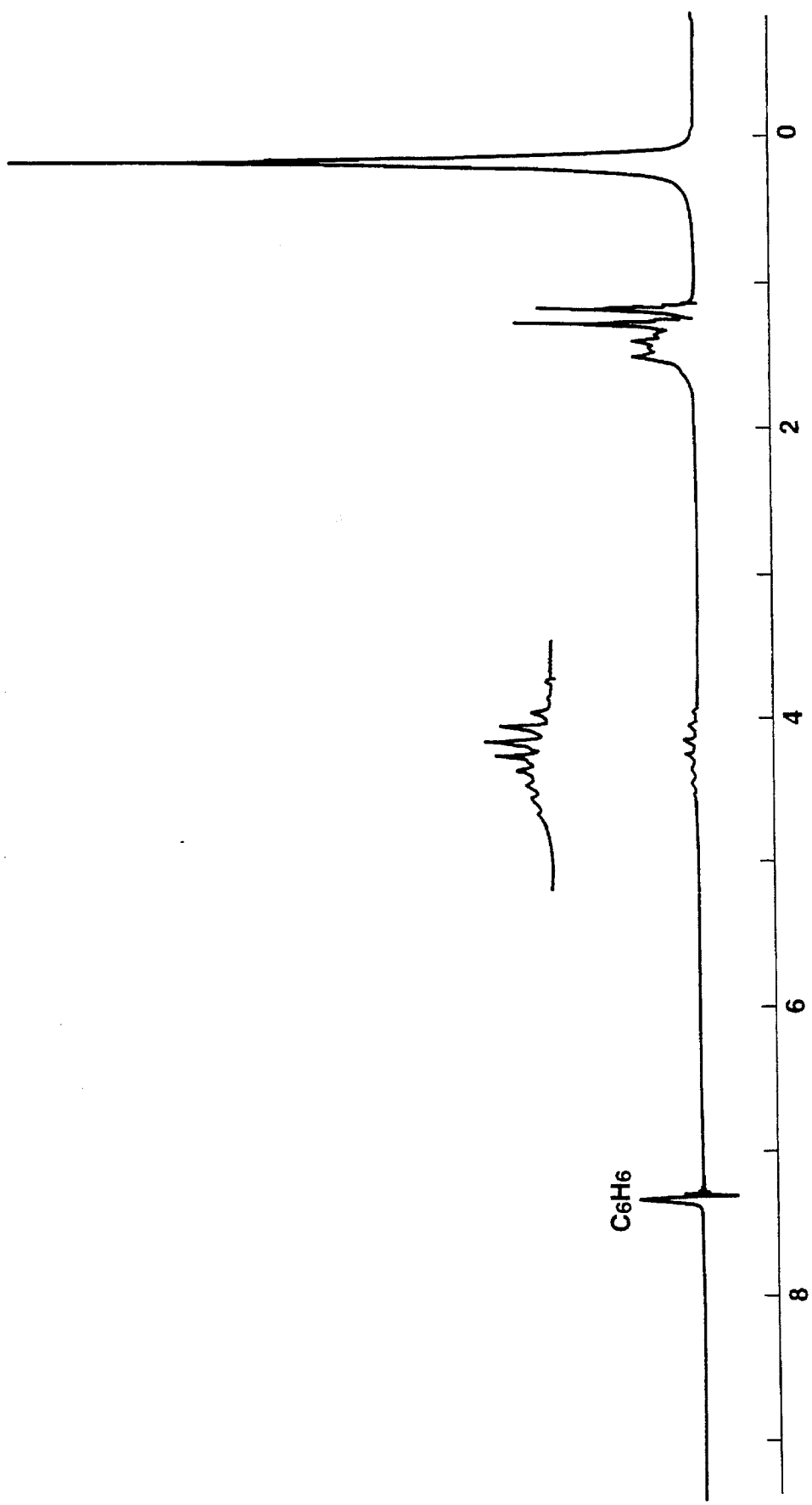
FIGS. 3 and 4 are $^1$H-NMR and IR spectra of the product of Example 2.
Figure 4:
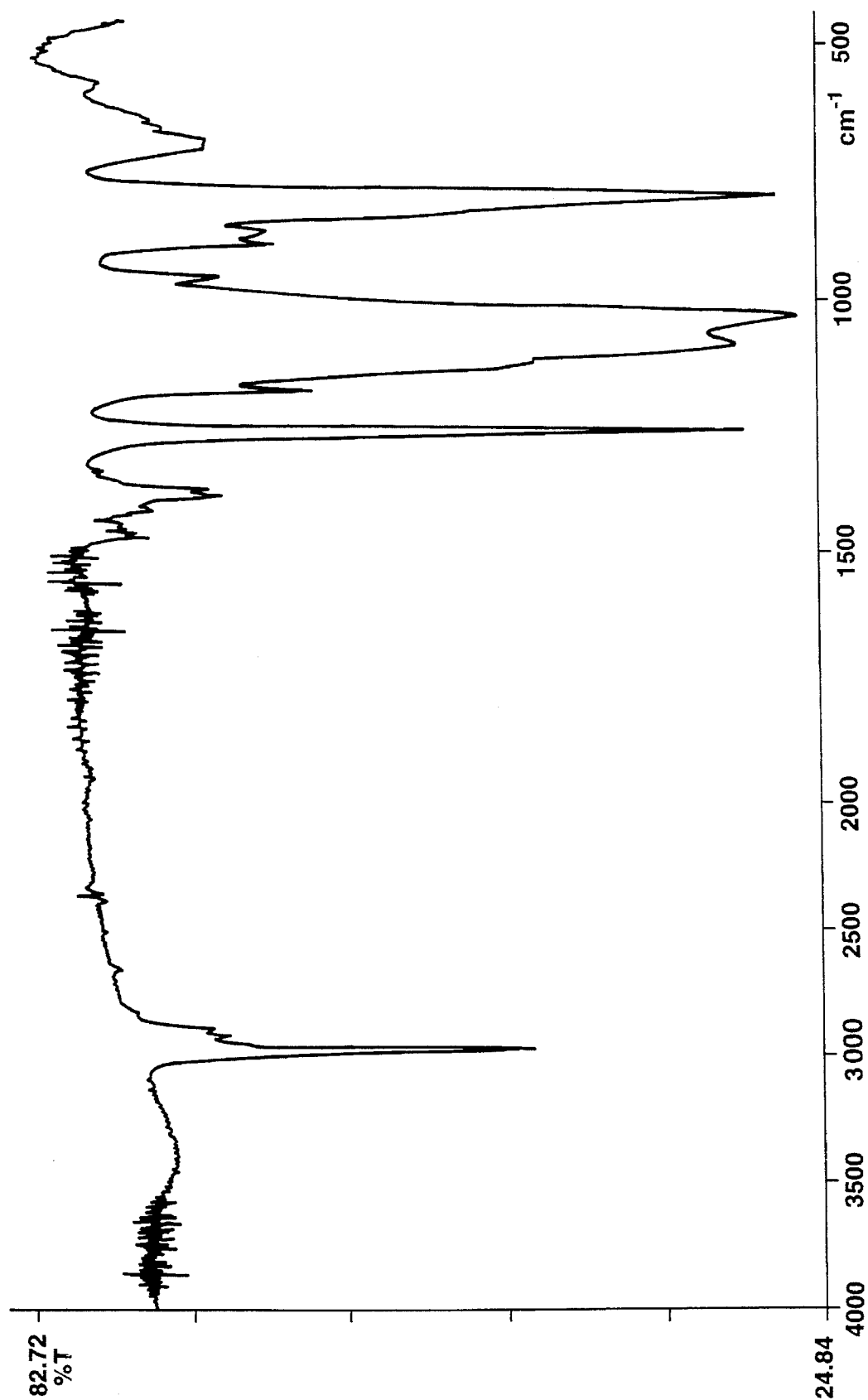

A 300-ml four-necked flask equipped with a stirrer, condenser, thermometer, and dropping funnel was charged with 88.8 grams of hexamethylcyclotrisiloxane and 27.3 grams of aluminum (III) triisopropoxide. In a nitrogen atmosphere, the contents were heated and stirred at 140° C. for 10 hours. After the disappearance of hexamethylcyclotrisiloxane was acknowledged by gas chromatography, the flask was cooled to room temperature. The volatiles were distilled off at 120° C. and 4 mmHg. The product (90.2 grams) was a clear liquid. On analysis of $^1$H-NMR spectrum (FIG. 3) and IR spectrum (FIG. 4), it was identified to be an aluminosiloxane having an Si—O—Al linkage in a molecule represented by the following average compositional formula.

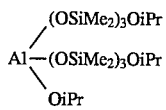

Example 3

Figure 5:
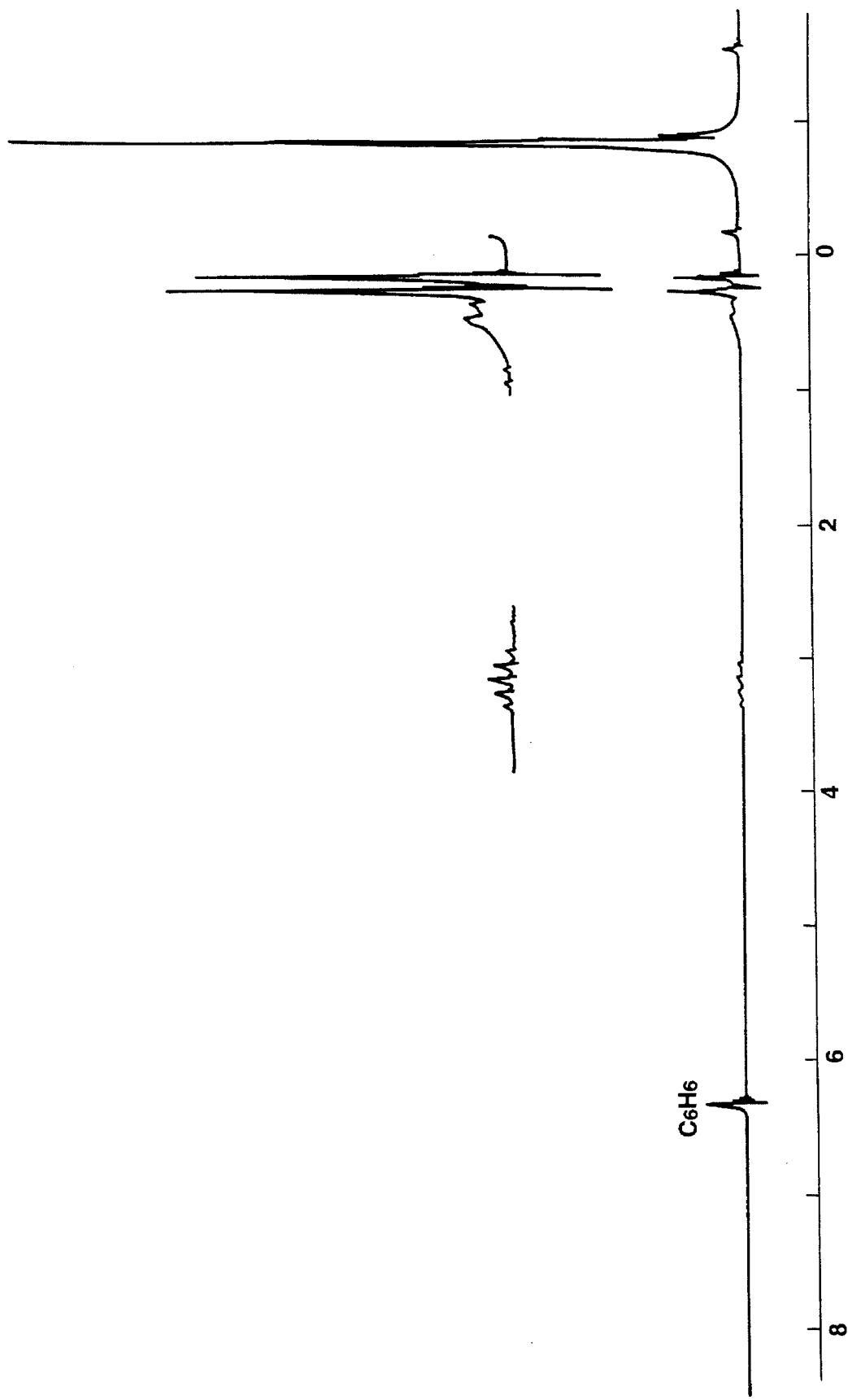
FIGS. 5 and 6 are $^1$H-NMR and IR spectra of the product of Example 3.
Figure 6:
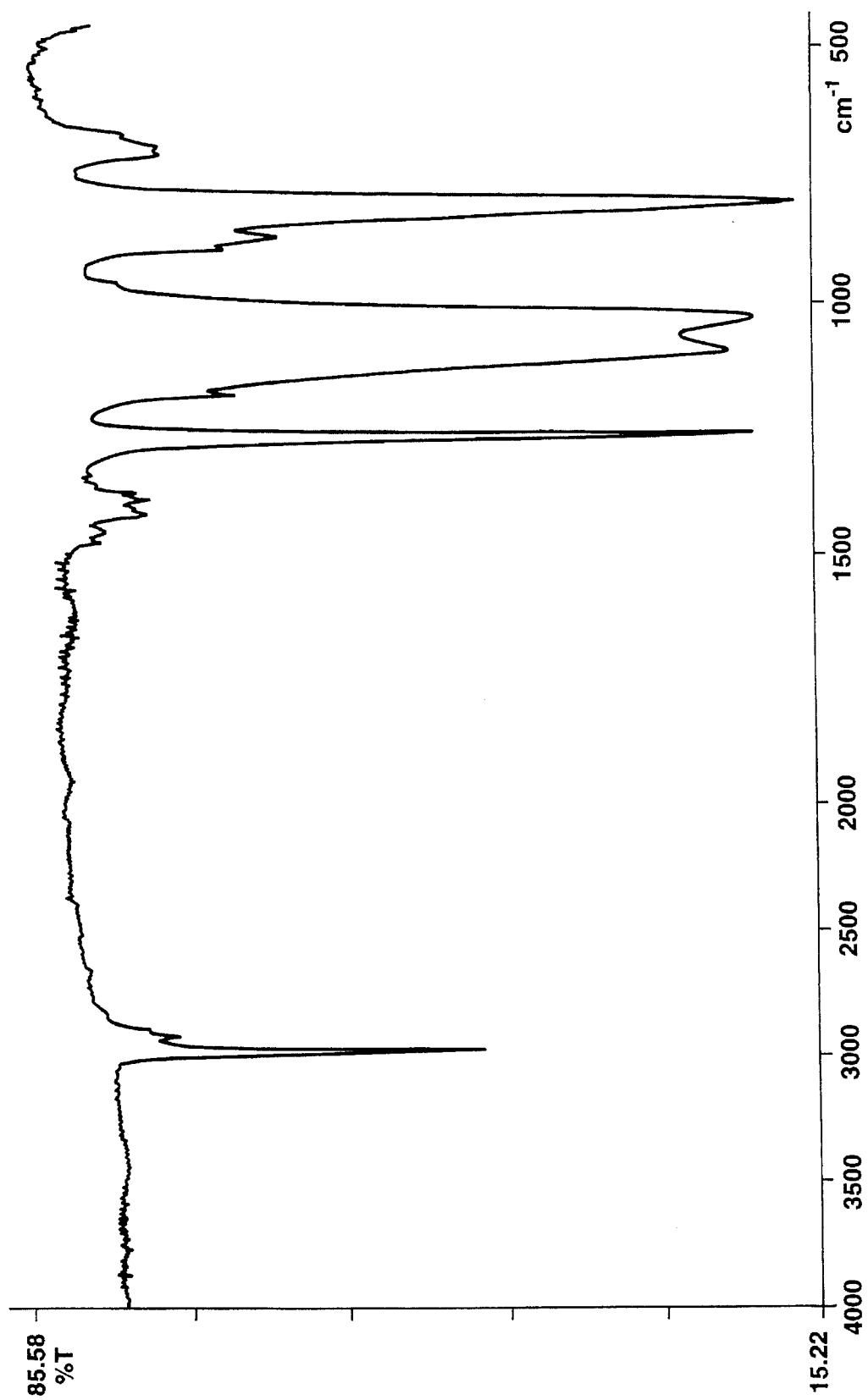

A 300-ml four-necked flask equipped with a stirrer, condenser, thermometer, and dropping funnel was charged with 111 grams of hexamethylcyclotrisiloxane and 20.4 grams of aluminum (III) triisopropoxide. In a nitrogen atmosphere, the contents were heated and stirred at 140° C. for 10 hours. After the disappearance of hexamethylcyclotrisiloxane was acknowledged by gas chromatography, the flask was cooled to room temperature. The volatiles were distilled off at 120° C. and 4 mmHg. The product (118 grams) was a clear liquid. On analysis of $^1$H-NMR spectrum (FIG. 5) and IR spectrum (FIG. 6), it was identified to be an aluminosiloxane having an Si—O—Al linkage in a molecule represented by the following average compositional formula.

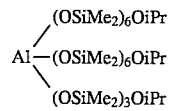

Example 4

Figure 7:
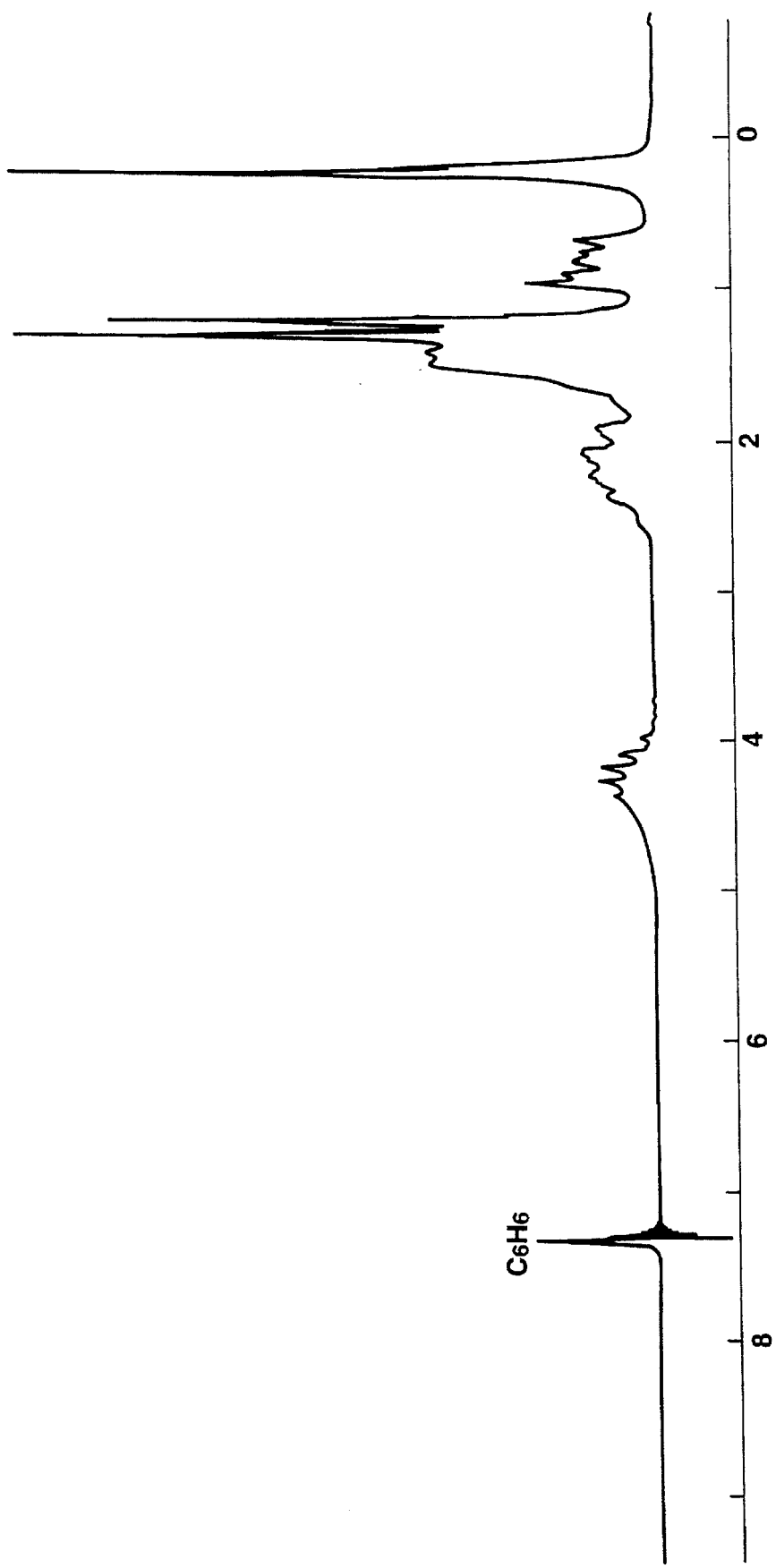
FIGS. 7 and 8 are $^1$H-NMR and IR spectra of the product of Example 4.
Figure 8:
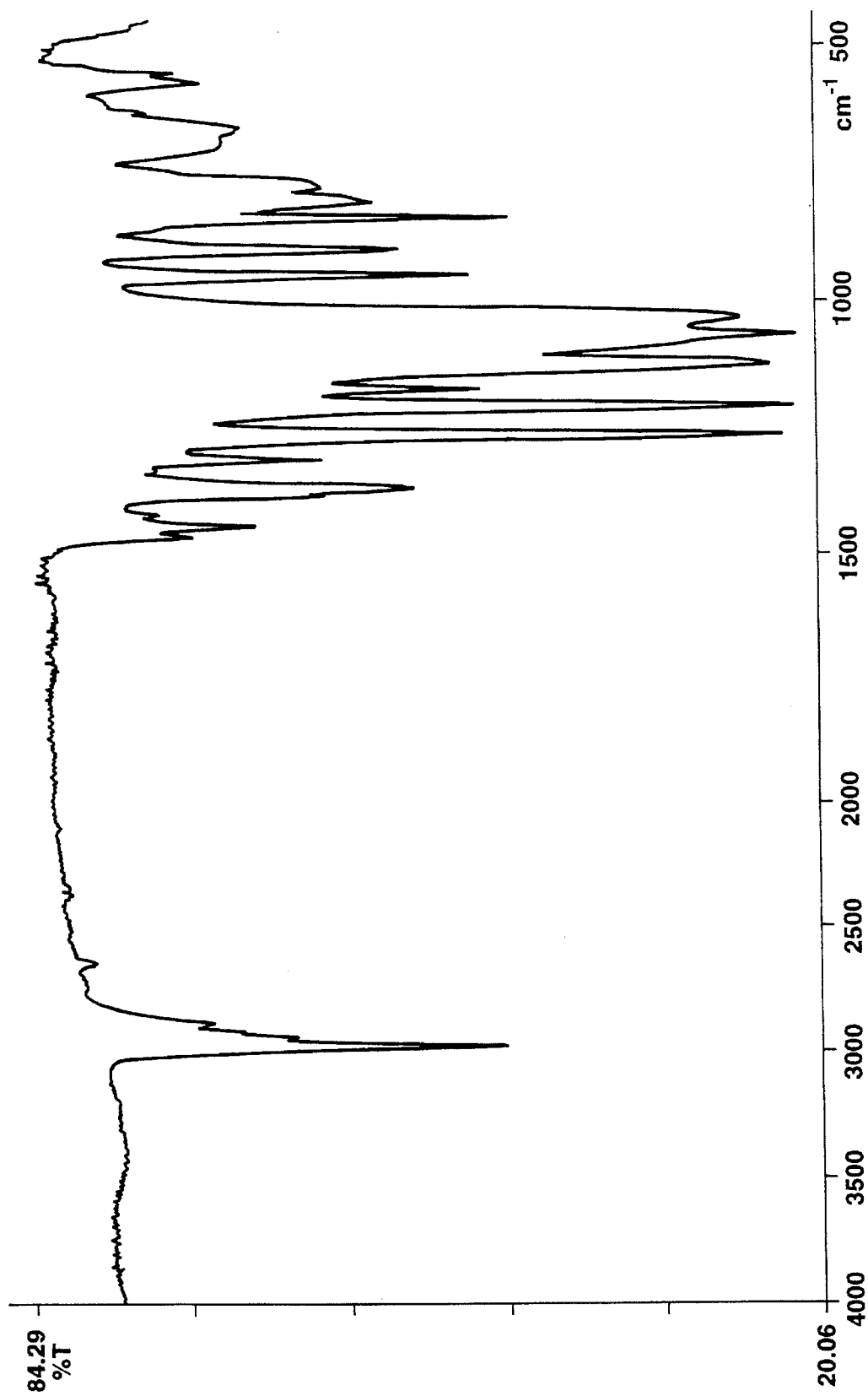

A 300-ml four-necked flask equipped with a stirrer, condenser, thermometer, and dropping funnel was charged with 88.0 grams of 1,3,5-tri(3,3,3-trifluoropropyl)-1,3,5-trimethylcyclotrisiloxane and 40.8 grams of aluminum (III) triisopropoxide. In a nitrogen atmosphere, the contents were heated and stirred at 140° C. for 10 hours. After the disappearance of 1,3,5-tri(3,3,3-trifluoropropyl)-1,3,5-trimethylcyclotrisiloxane was acknowledged by gas chromatography, the flask was cooled to room temperature. The volatiles were distilled off at 120° C. and 4 mmHg. The product (103 grams) was a clear liquid. On analysis of $^1$H-NMR spectrum (FIG. 7) and IR spectrum (FIG. 8), it was identified to be an aluminosiloxane having an Si—O—Al linkage in a molecule represented by the following average compositional formula.

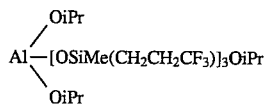

Example 5

Figure 9:
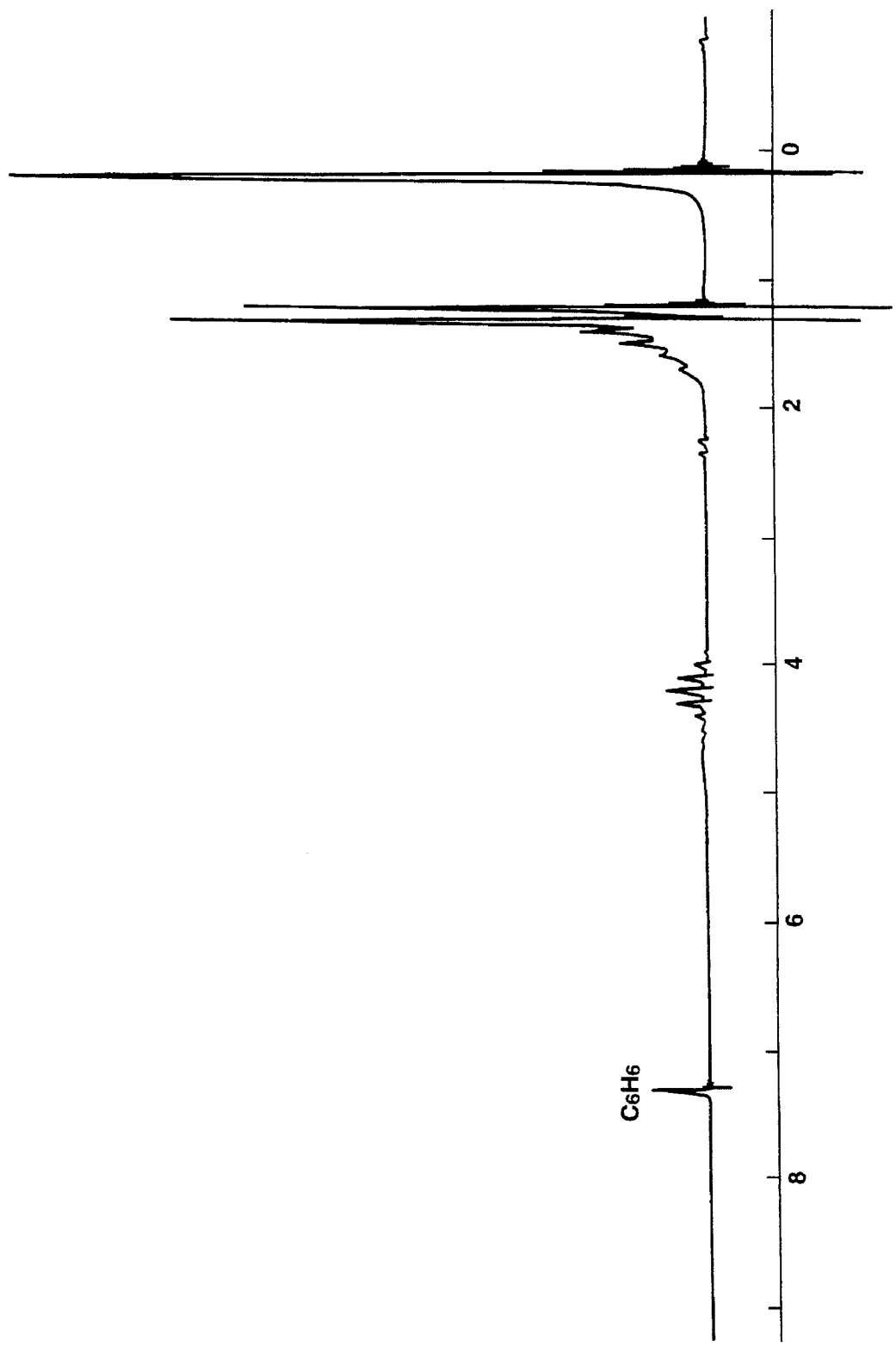
FIGS. 9 and 10 are $^1$H-NMR and IR spectra of the product of Example 5.
Figure 10:
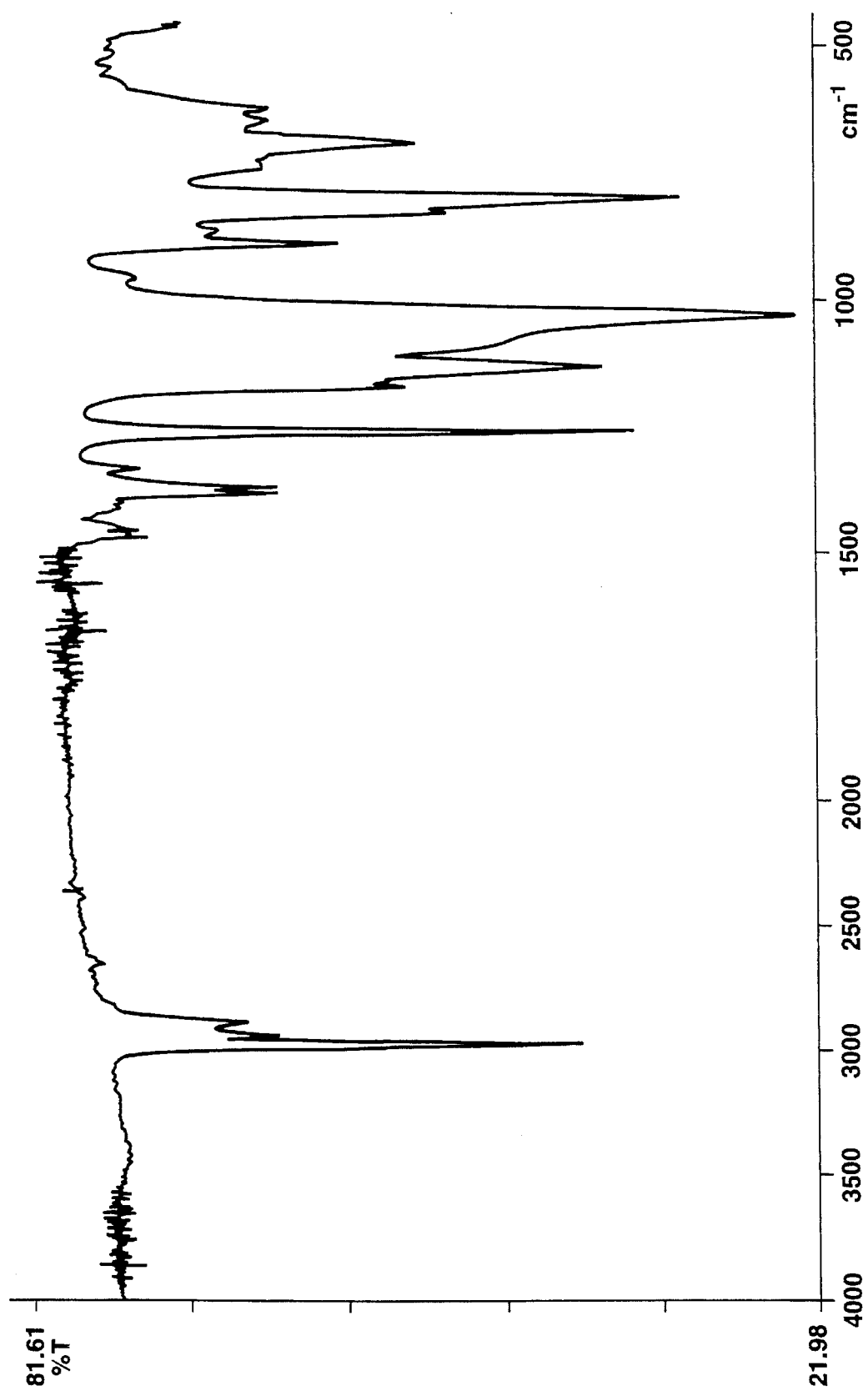

A 300-ml four-necked flask equipped with a stirrer, condenser, thermometer, and dropping funnel was charged with 66.6 grams of hexamethylcyclotrisiloxane, which was heated to 80° C. in a nitrogen atmosphere. To the flask, 85.2 grams of titanium (IV) tetraisopropoxide was added dropwise. The contents were stirred at 100° C. for 8 hours. After the disappearance of hexamethylcyclotrisiloxane was acknowledged by gas chromatography, the flask was cooled to room temperature. The volatiles were distilled off at 120° C. and 4 mmHg. The product (120 grams) was a yellow clear liquid. On analysis of $^1$H-NMR spectrum (FIG. 9) and IR spectrum (FIG. 10), it was identified to be a titanosiloxane having an Si—O—Ti linkage in a molecule represented by the following average compositional formula.

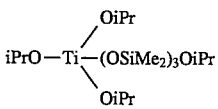

Example 6

Figure 11:
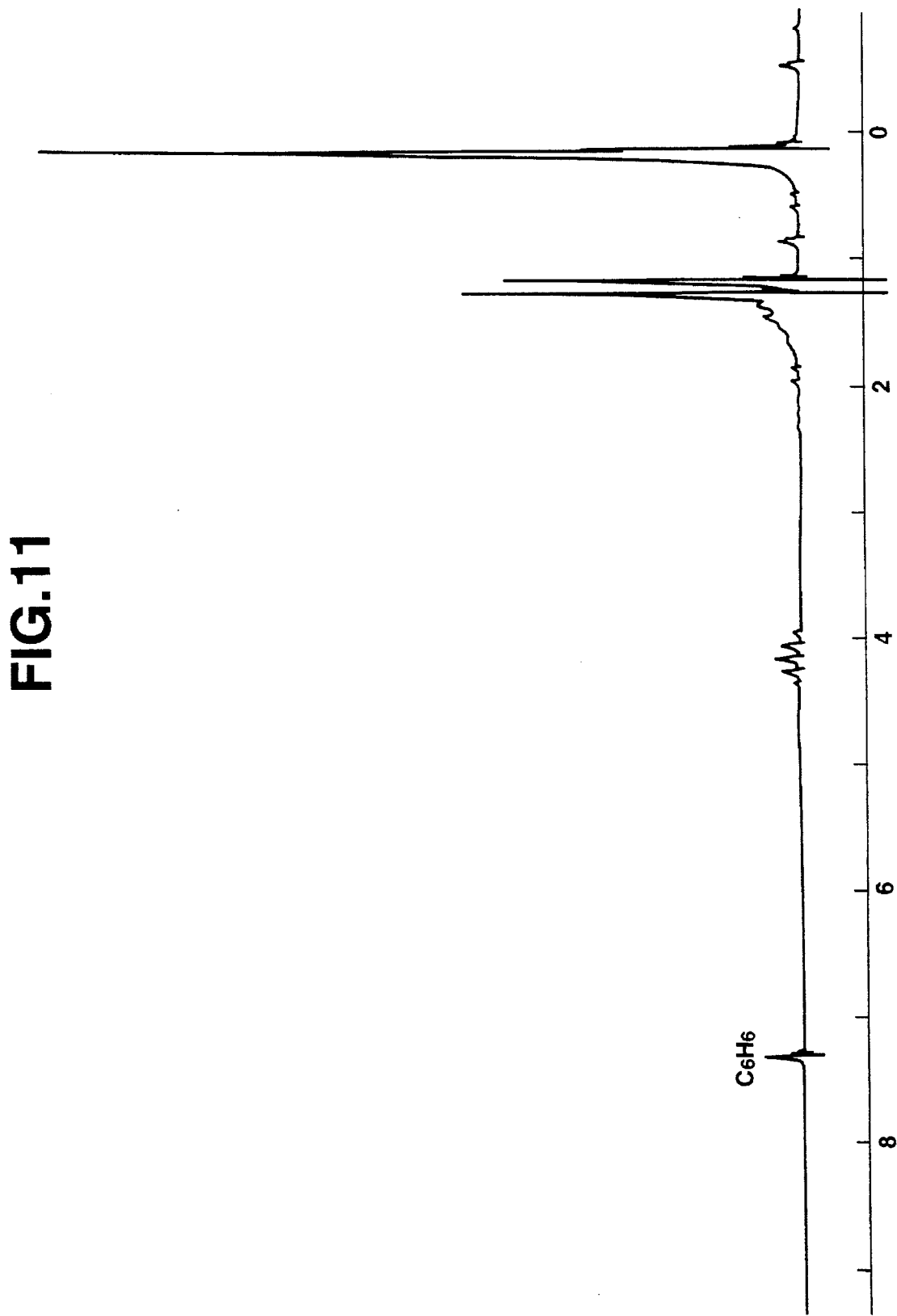
FIGS. 11 and 12 are $^1$H-NMR and IR spectra of the product of Example 6.
Figure 12:
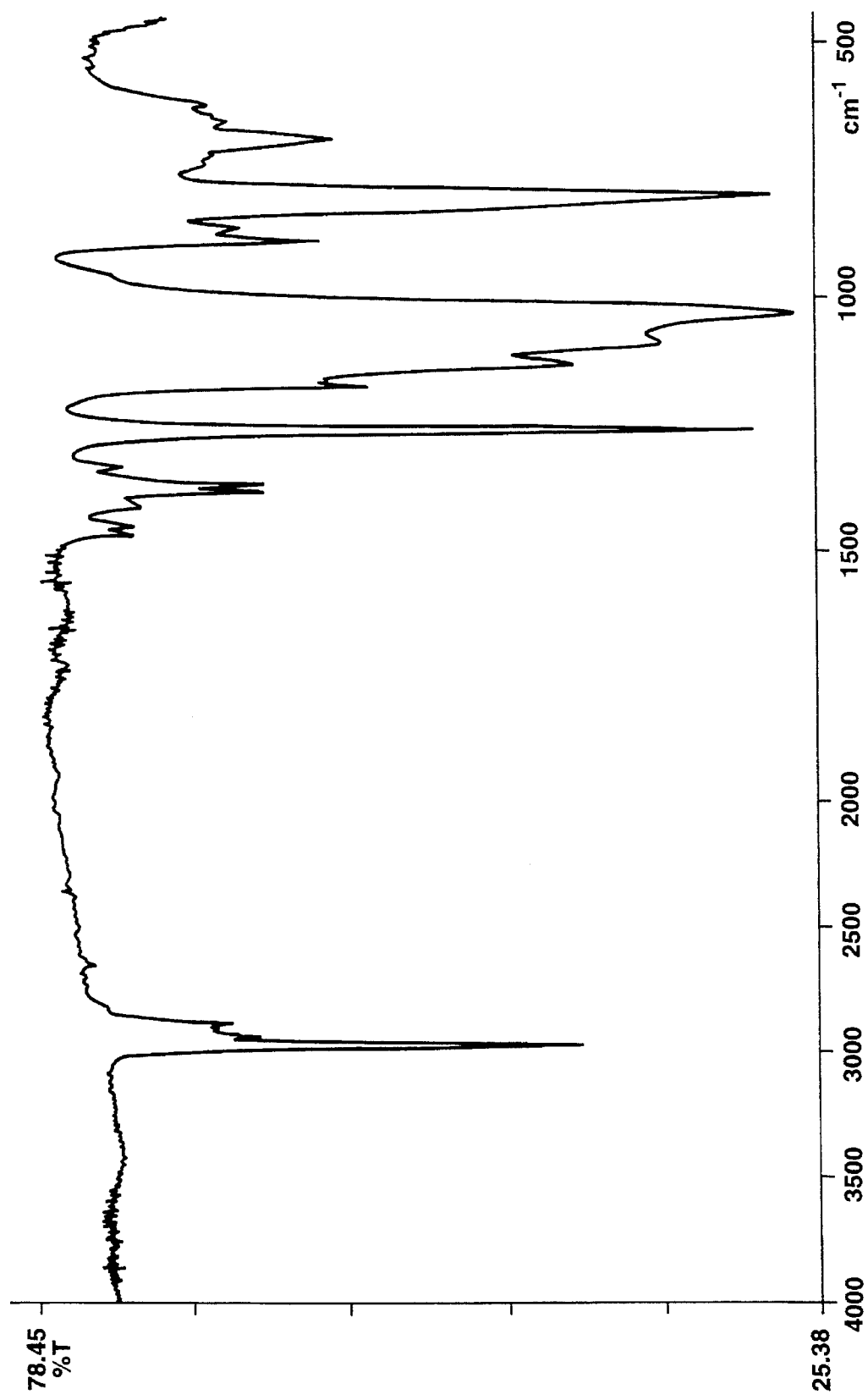

A 300-ml four-necked flask equipped with a stirrer, condenser, thermometer, and dropping funnel was charged with 88.8 grams of hexamethylcyclotrisiloxane, which was heated to 80° C. in a nitrogen atmosphere. To the flask, 56.8 grams of titanium (IV) tetraisopropoxide was added dropwise. The contents were stirred at 100° C. for 8 hours. After the disappearance of hexamethylcyclotrisiloxane was acknowledged by gas chromatography, the flask was cooled to room temperature. The volatiles were distilled off at 120° C. and 4 mmHg. The product (122 grams) was a yellow clear liquid. On analysis of $^1$H-NMR spectrum (FIG. 11) and IR spectrum (FIG. 12), it was identified to be a titanosiloxane having an Si—O—Ti linkage in a molecule represented by the following average compositional formula.

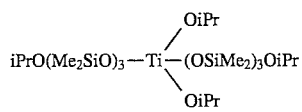

Example 7

Figure 13:
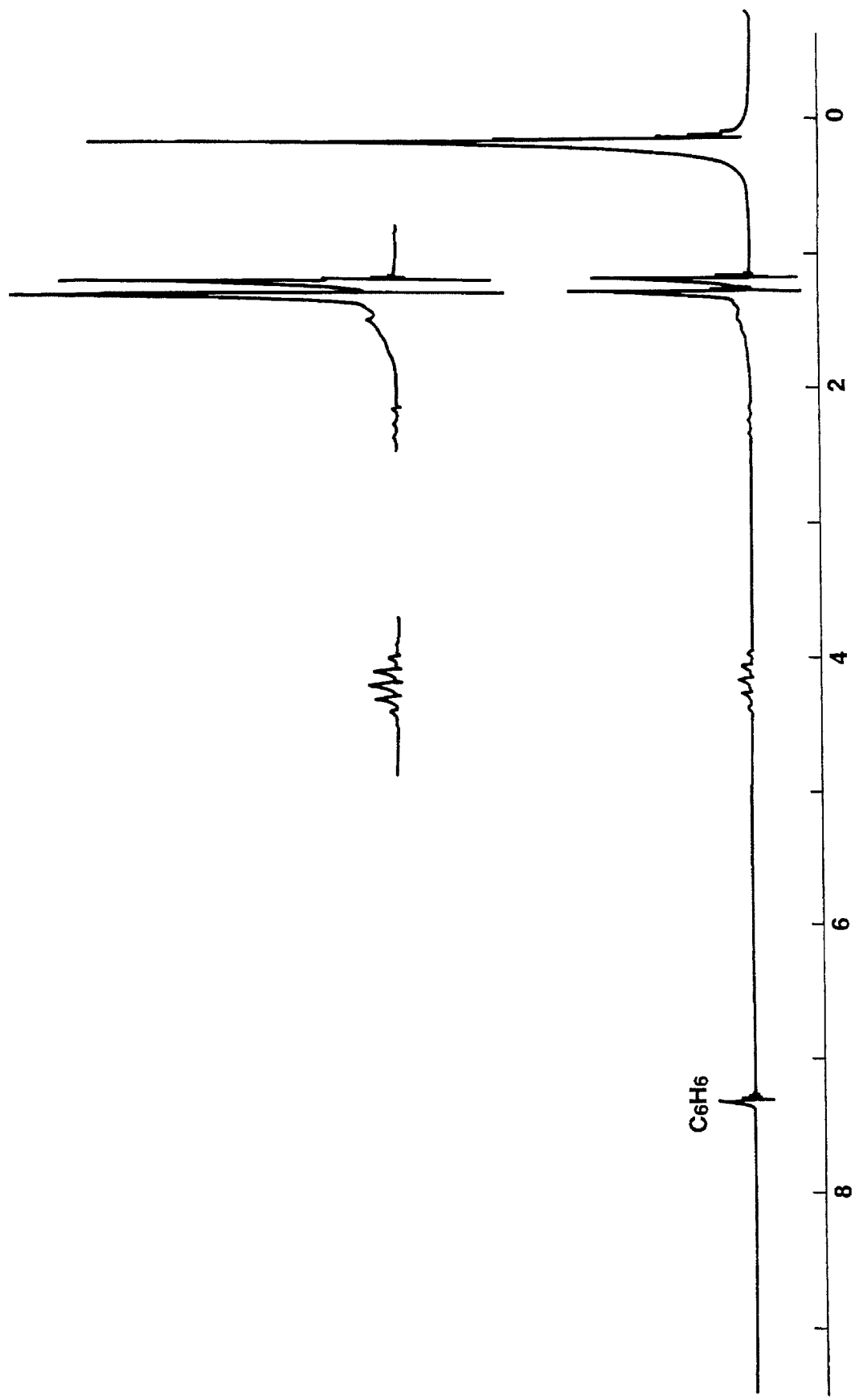
FIGS. 13 and 14 are $^1$H-NMR and IR spectra of the product of Example 7.
Figure 14:
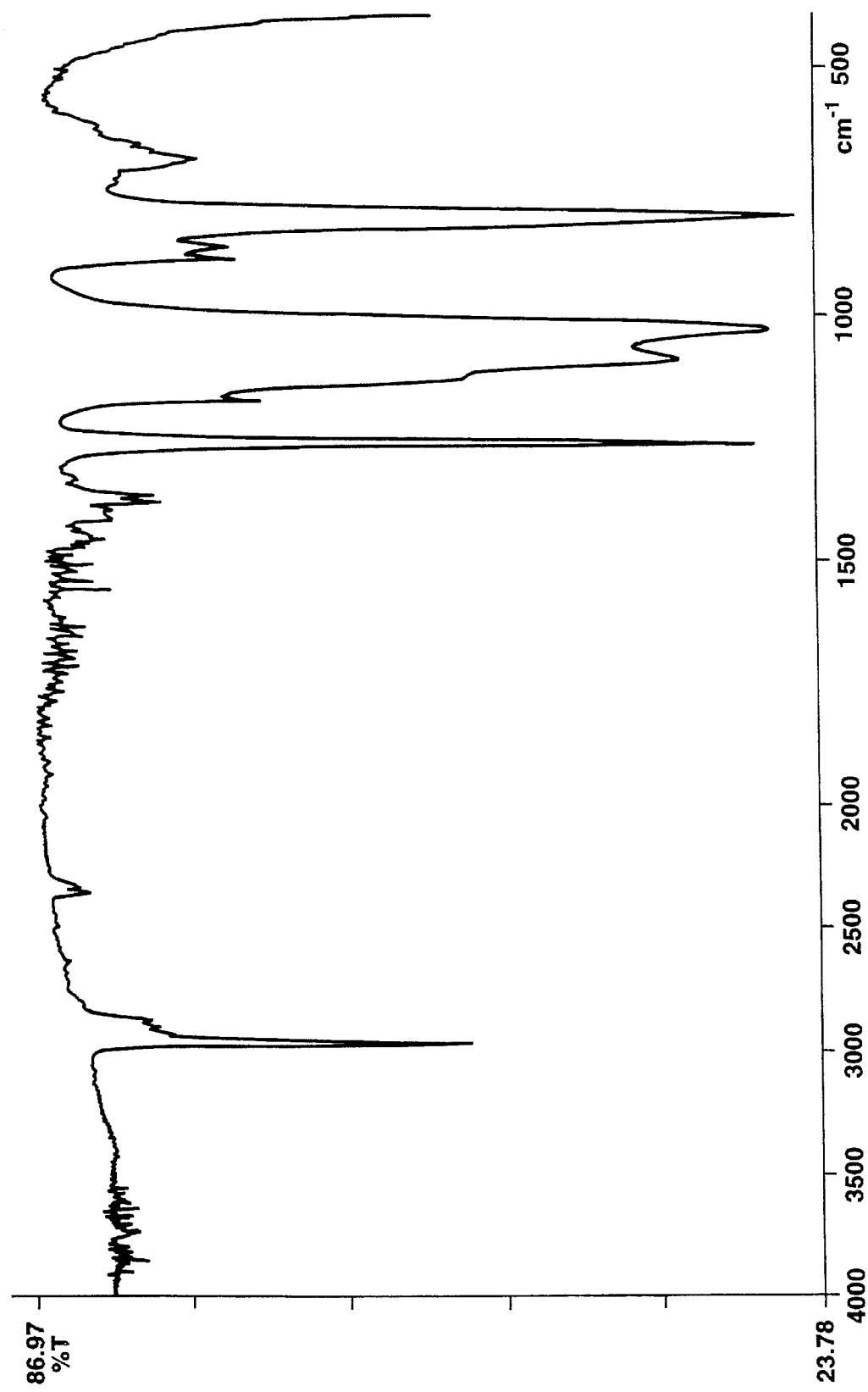

A 300-ml four-necked flask equipped with a stirrer, condenser, thermometer, and dropping funnel was charged with 178 grams of hexamethylcyclotrisiloxane, which was heated to 80° C. in a nitrogen atmosphere. To the flask, 56.8 grams of titanium (IV) tetraisopropoxide was added dropwise. The contents were heated and stirred at 100° C. for 8 hours. After the disappearance of hexamethylcyclotrisiloxane was acknowledged by gas chromatography, the flask was cooled to room temperature. The volatiles were distilled off at 120° C. and 4 mmHg. The product (199 grams) was a yellow clear liquid. On analysis of $^1$H-NMR spectrum (FIG. 13) and IR spectrum (FIG. 14), it was identified to be a titanosiloxane having an Si—O—Ti linkage in a molecule represented by the following average compositional formula.

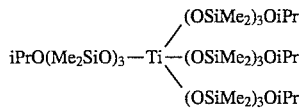

Example 8

Figure 15:
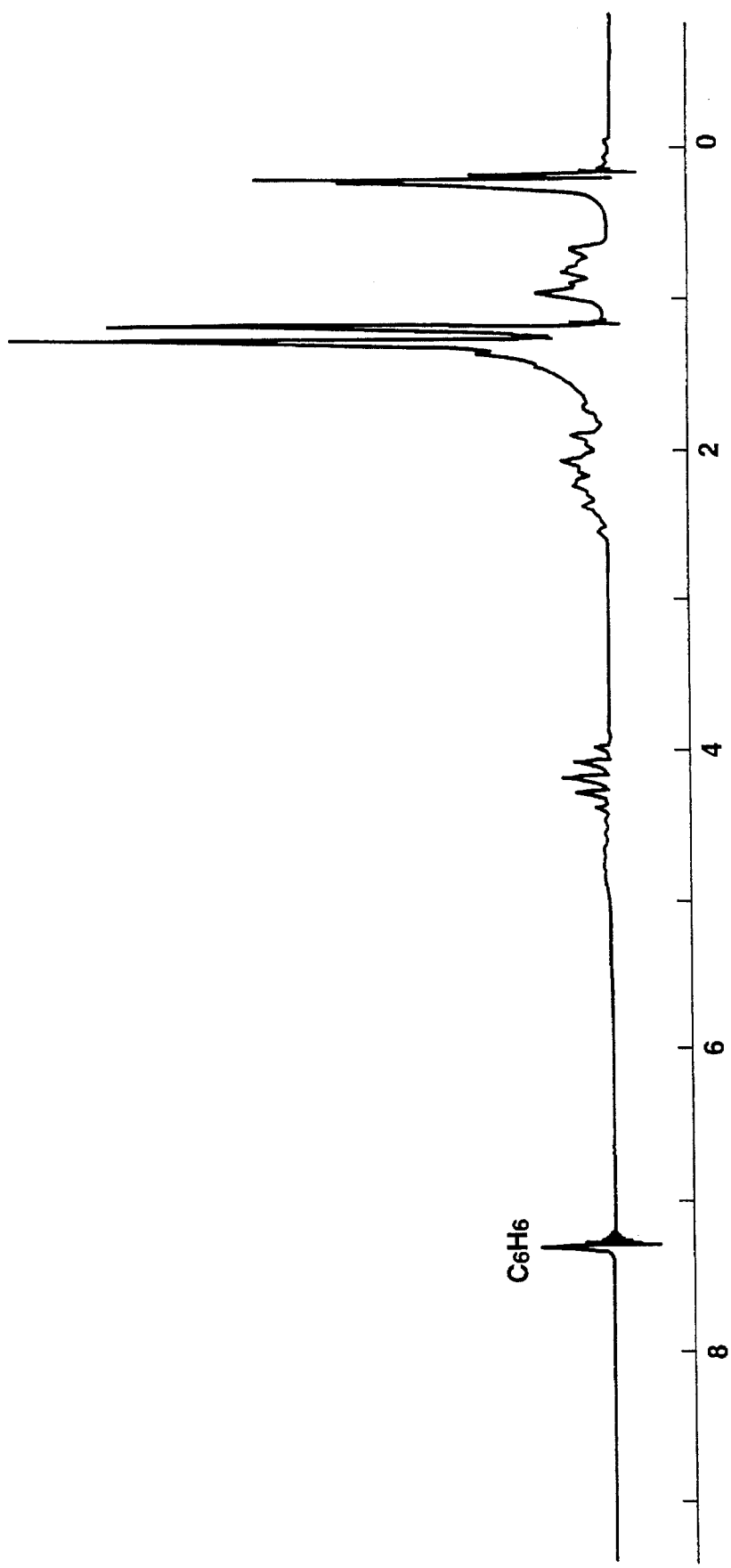
FIGS. 15 and 16 are $^1$H-NMR and IR spectra of the product of Example 8.
Figure 16:
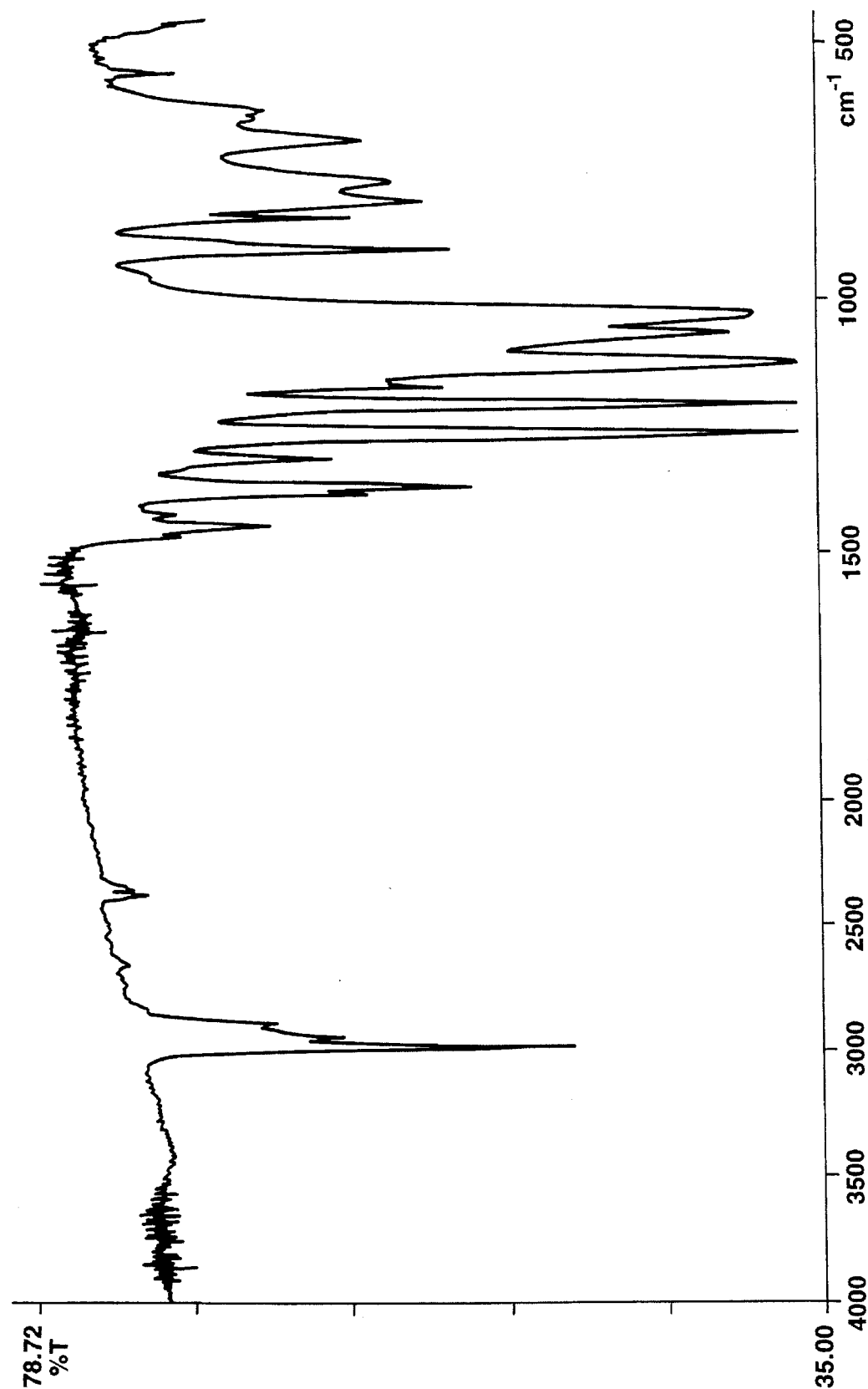

A 300-ml four-necked flask equipped with a stirrer, condenser, thermometer, and dropping funnel was charged with 44.0 grams of 1,3,5-tri(3,3,3-trifluoropropyl)-1,3,5-trimethylcyclotrisiloxane, which was heated to 120° C. in a nitrogen atmosphere. To the flask, 28.4 grams of titanium (IV) tetraisopropoxide was added dropwise. The contents were heated and stirred at 80° C. for 6 hours. After the disappearance of 1,3,5-tri(3,3,3-trifluoropropyl)-1,3,5-trimethylcyclotrisiloxane was acknowledged by gas chromatography, the flask was cooled to room temperature. The volatiles were distilled off at 120° C. and 4 mmHg. The product (61.5 grams) was a yellow clear liquid. On analysis of $^1$H-NMR spectrum (FIG. 15) and IR spectrum (FIG. 16), it was identified to be a titanosiloxane having an Si—O—Ti linkage in a molecule represented by the following average compositional formula.

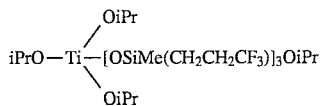

Example 9

Figure 17:
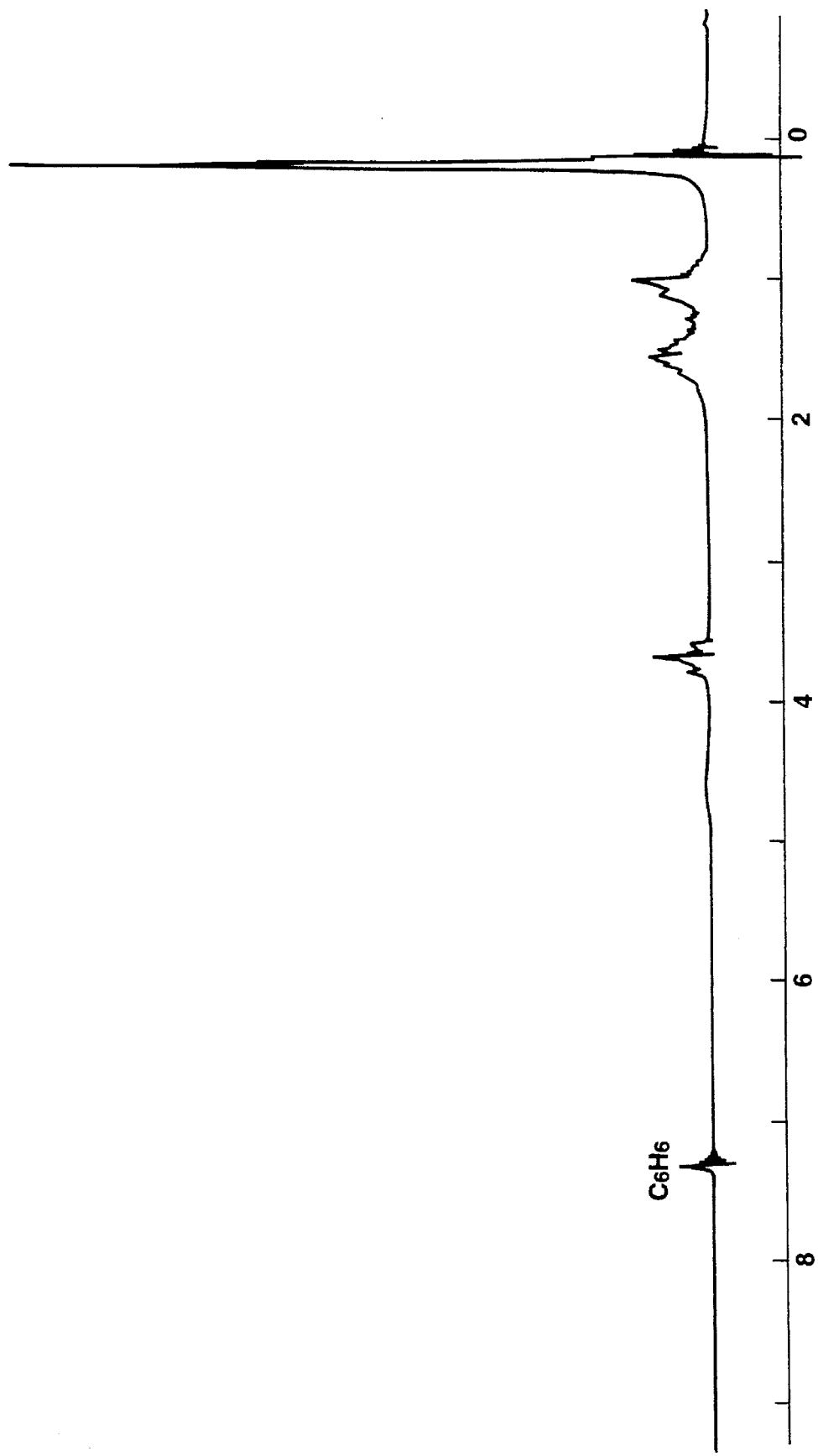
FIGS. 17 and 18 are $^1$H-NMR and IR spectra of the product of Example 9.
Figure 18:
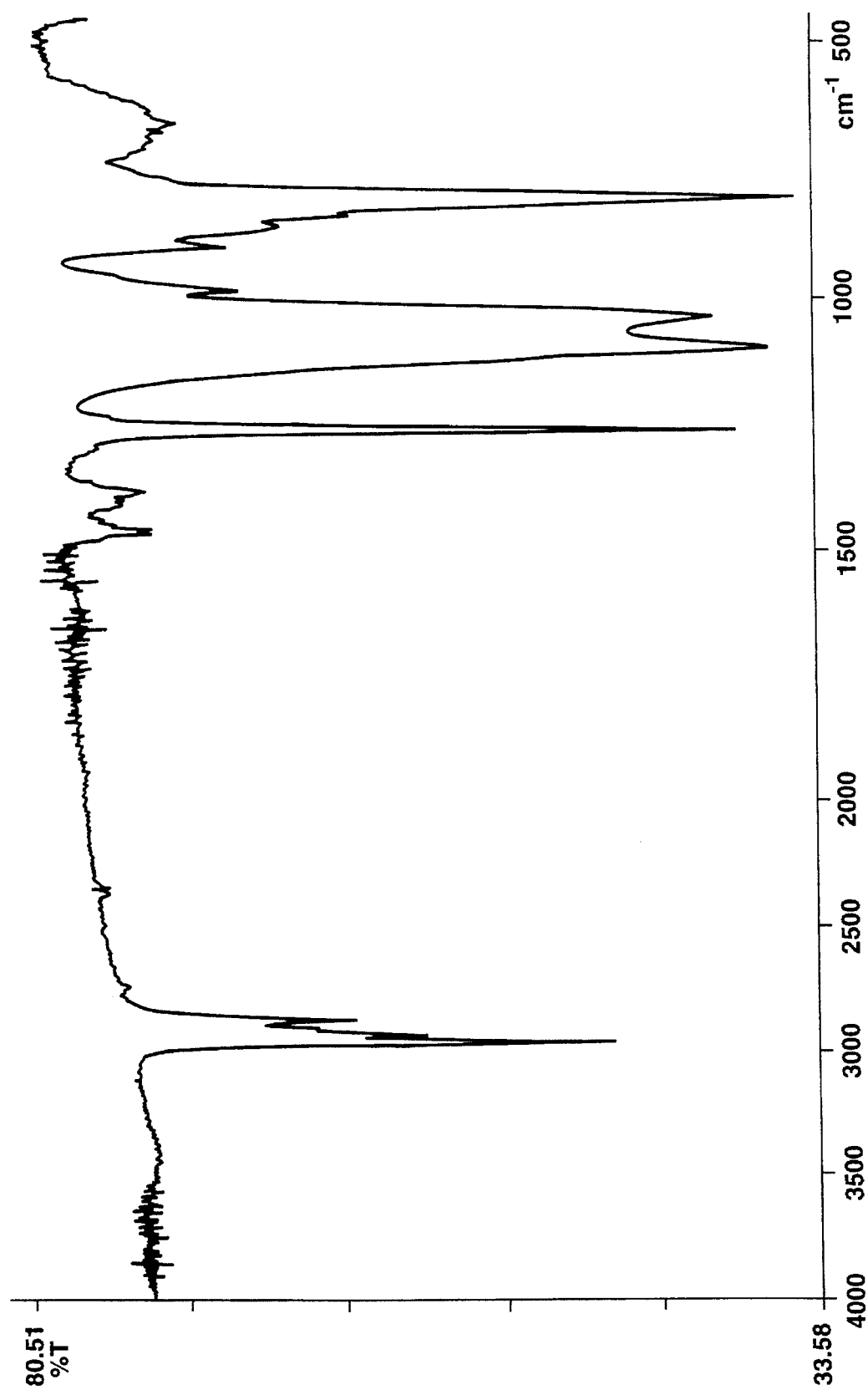

A 300-ml four-necked flask equipped with a stirrer, condenser, thermometer, and dropping funnel was charged with 66.6 grams of hexamethylcyclotrisiloxane, which was heated to 80° C. in a nitrogen atmosphere. To the flask, 51.0 grams of titanium (IV) tetra-n-butoxide was added dropwise. The contents were heated and stirred at 160° C. for 8 hours. After the disappearance of hexamethylcyclotrisiloxane was acknowledged by gas chromatography, the flask was cooled to room temperature. The volatiles were distilled off at 120° C. and 4 mmHg. The product (96.8 grams) was a yellow clear liquid. On analysis of $^1$H-NMR spectrum (FIG. 17) and IR spectrum (FIG. 18), it was identified to be a titanosiloxane having an Si—O—Ti linkage in a molecule represented by the following average compositional formula.

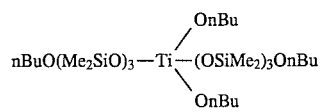

Example 10

Figure 19:
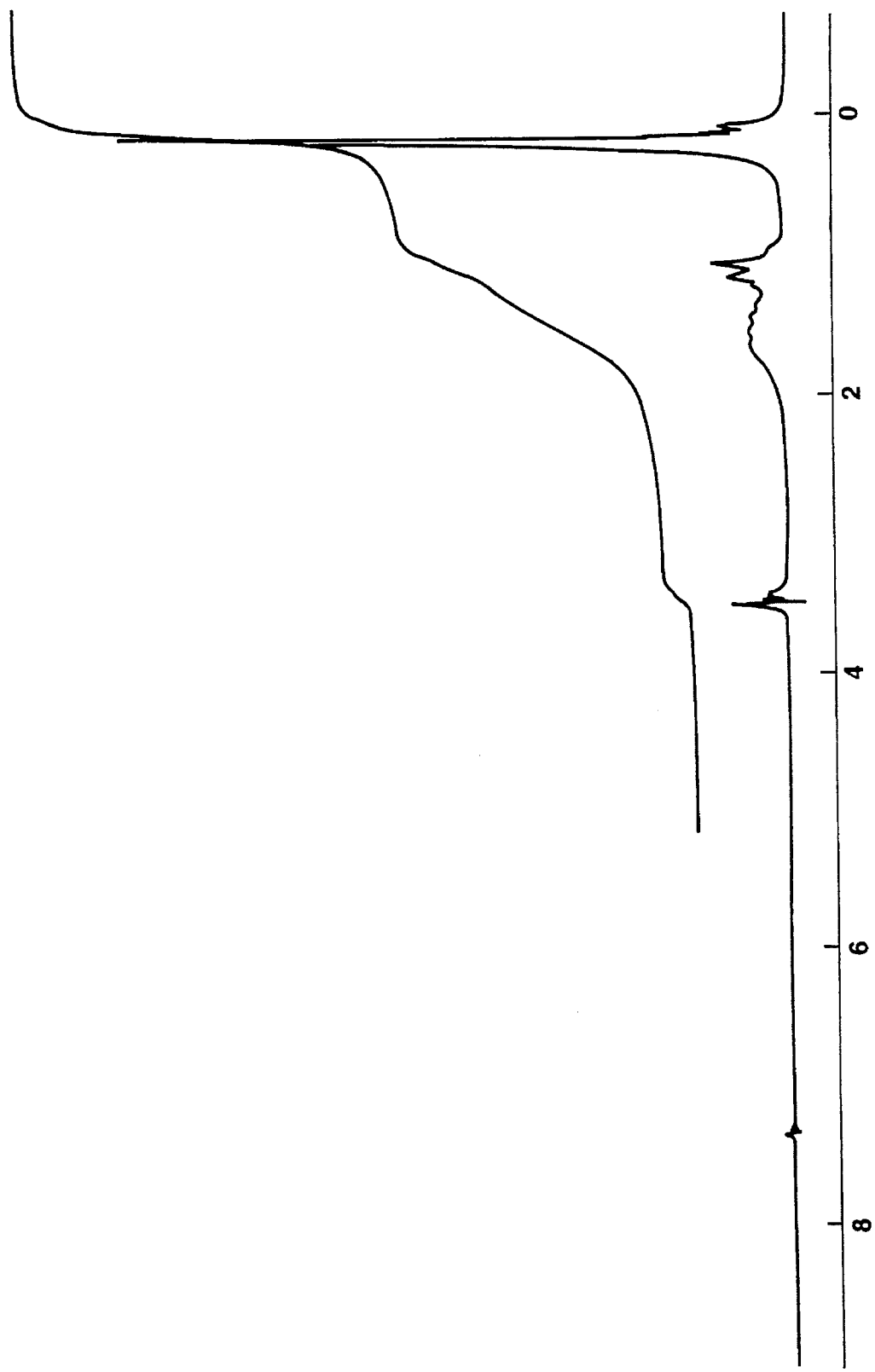
FIGS. 19 and 20 are $^1$H-NMR and IR spectra of the stannosiloxane of Example 10.
Figure 20:
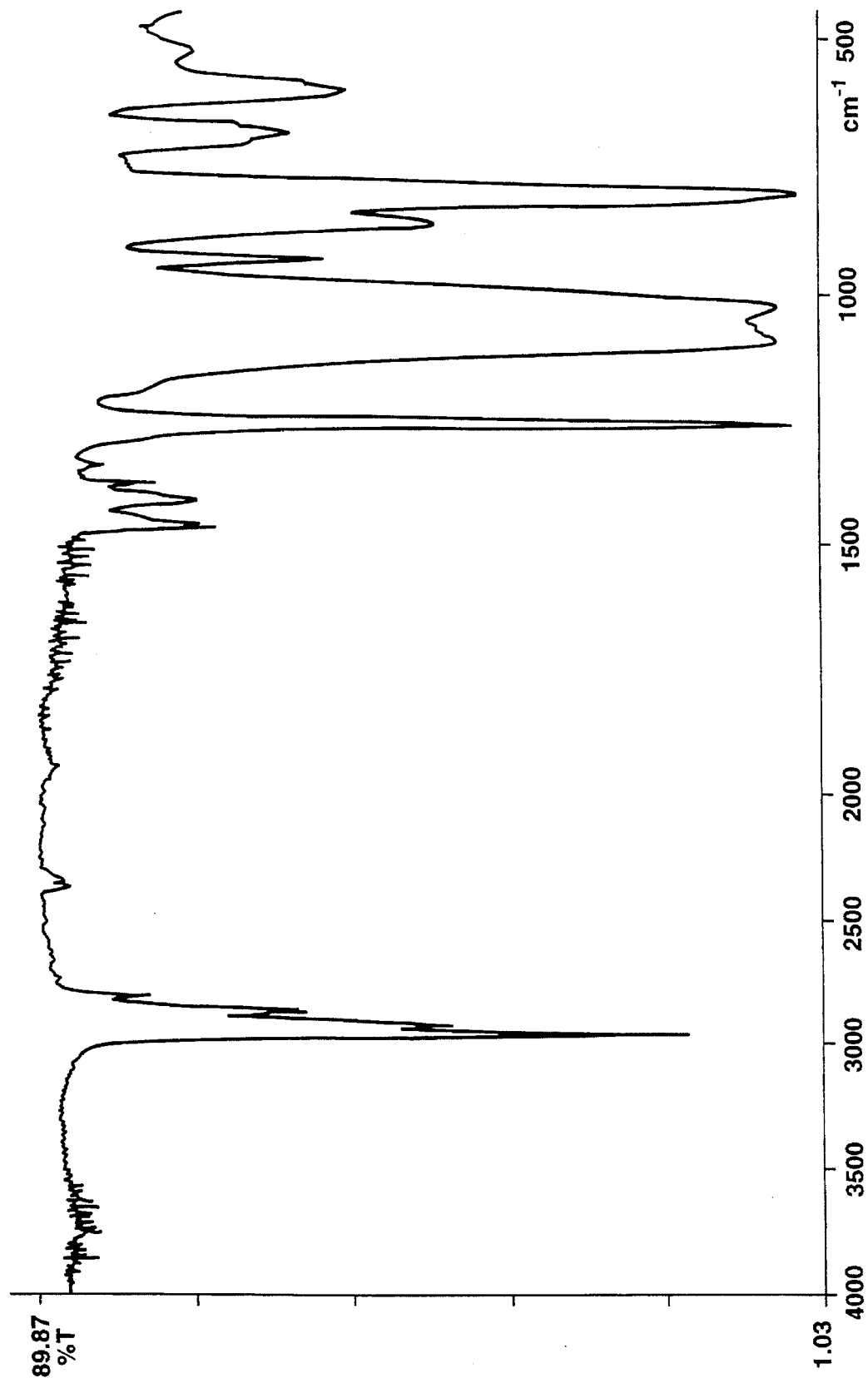

A 500-ml four-necked flask equipped with a stirrer, condenser, thermometer, and dropping funnel was charged with 267 grams of hexamethylcyclotrisiloxane, which was heated to 80° C. in a nitrogen atmosphere. To the flask, 177 grams of dibutyltin dimethoxide was added dropwise. The contents were heated and stirred at 80° C. for 4 hours. After the disappearance of hexamethylcyclotrisiloxane was acknowledged by gas chromatography, the volatiles were distilled off at 120° C. and 4 mmHg. The product (368 grams) was a liquid having a viscosity of 325 centipoise. On analysis of $^1$H-NMR spectrum (FIG. 19) and IR spectrum (FIG. 20), it was identified to be a stannosiloxane represented by the following average compositional formula.

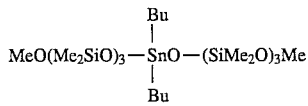

Example 11

Figure 21:
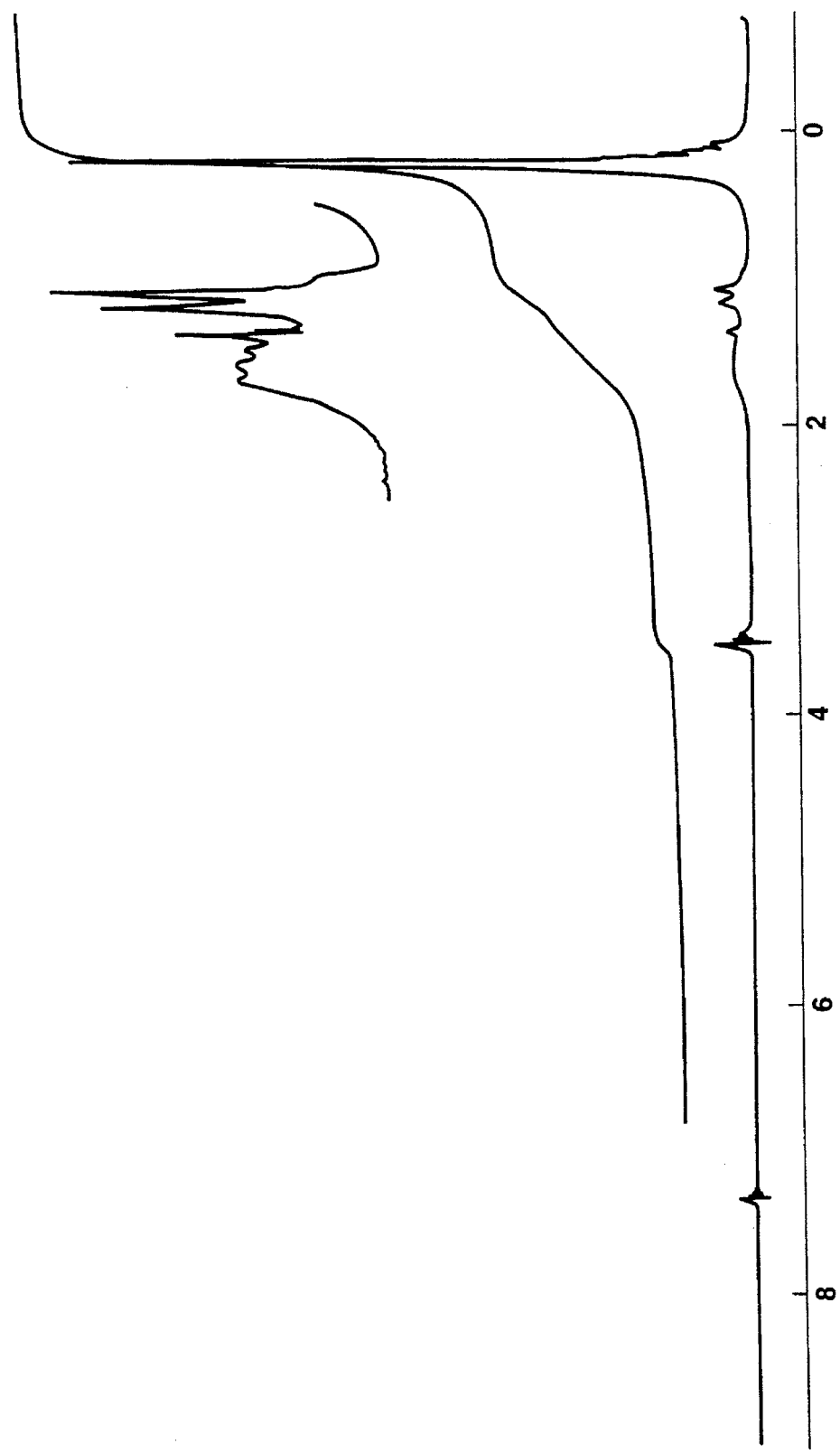
FIGS. 21 and 22 are $^1$H-NMR and IR spectra of the stannosiloxane of Example 11.
Figure 22:
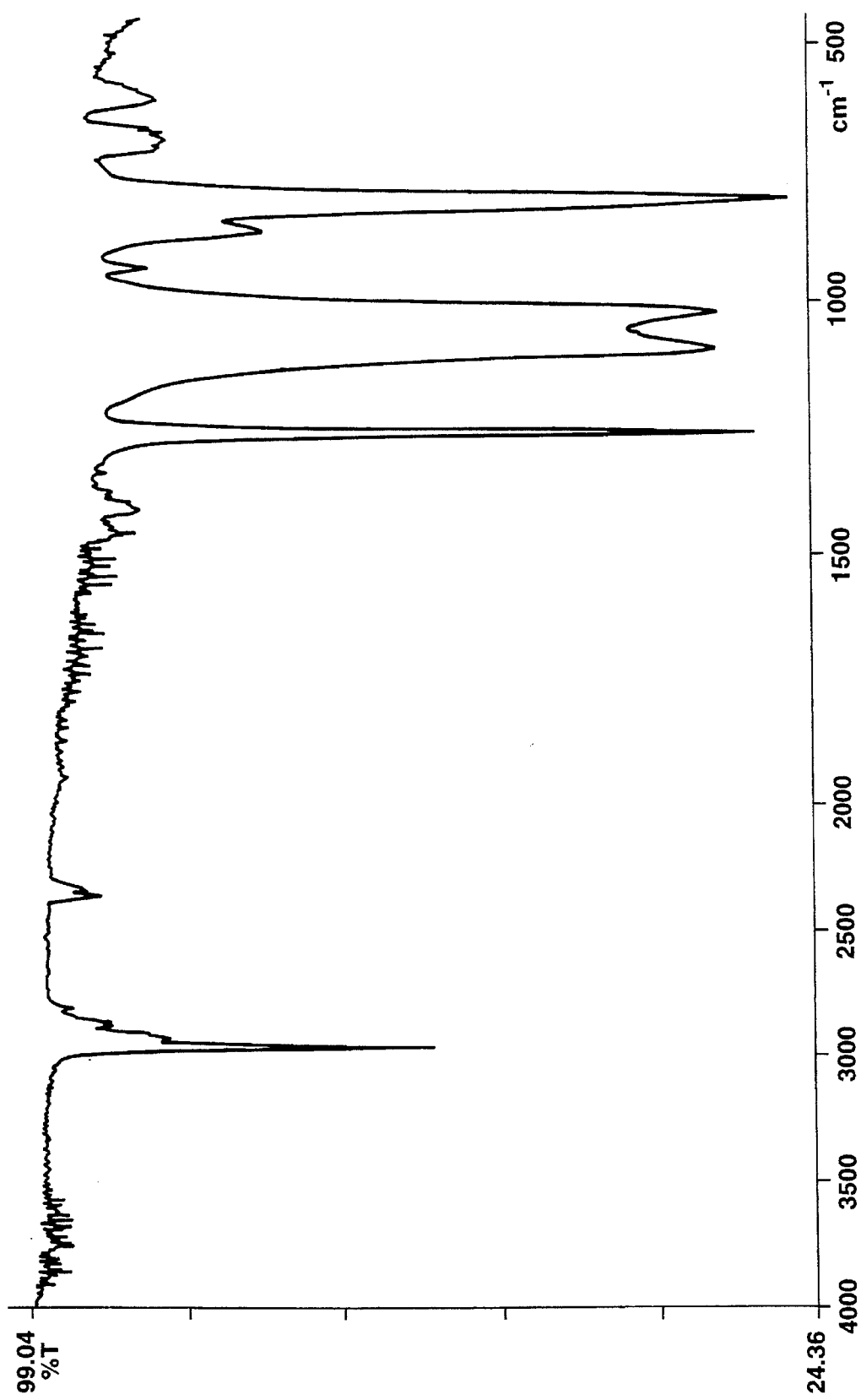

A 300-ml four-necked flask equipped with a stirrer, condenser, thermometer, and dropping funnel was charged with 178 grams of hexamethylcyclotrisiloxane, which was heated to 80° C. in a nitrogen atmosphere. To the flask, 59.6 grams of dibutyltin dimethoxide was added dropwise. The contents were stirred at 80° C. for 4 hours. After the disappearance of hexamethylcyclotrisiloxane was acknowledged by gas chromatography, the volatiles were distilled off at 120° C. and 4 mmHg. The product (214 grams) was a liquid having a viscosity of 244 centipoise. On analysis of $^1$H-NMR spectrum (FIG. 21) and IR spectrum (FIG. 22), it was identified to be a stannosiloxane represented by the following average compositional formula.

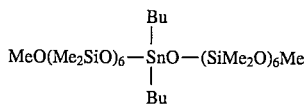

Example 12

Figure 23:
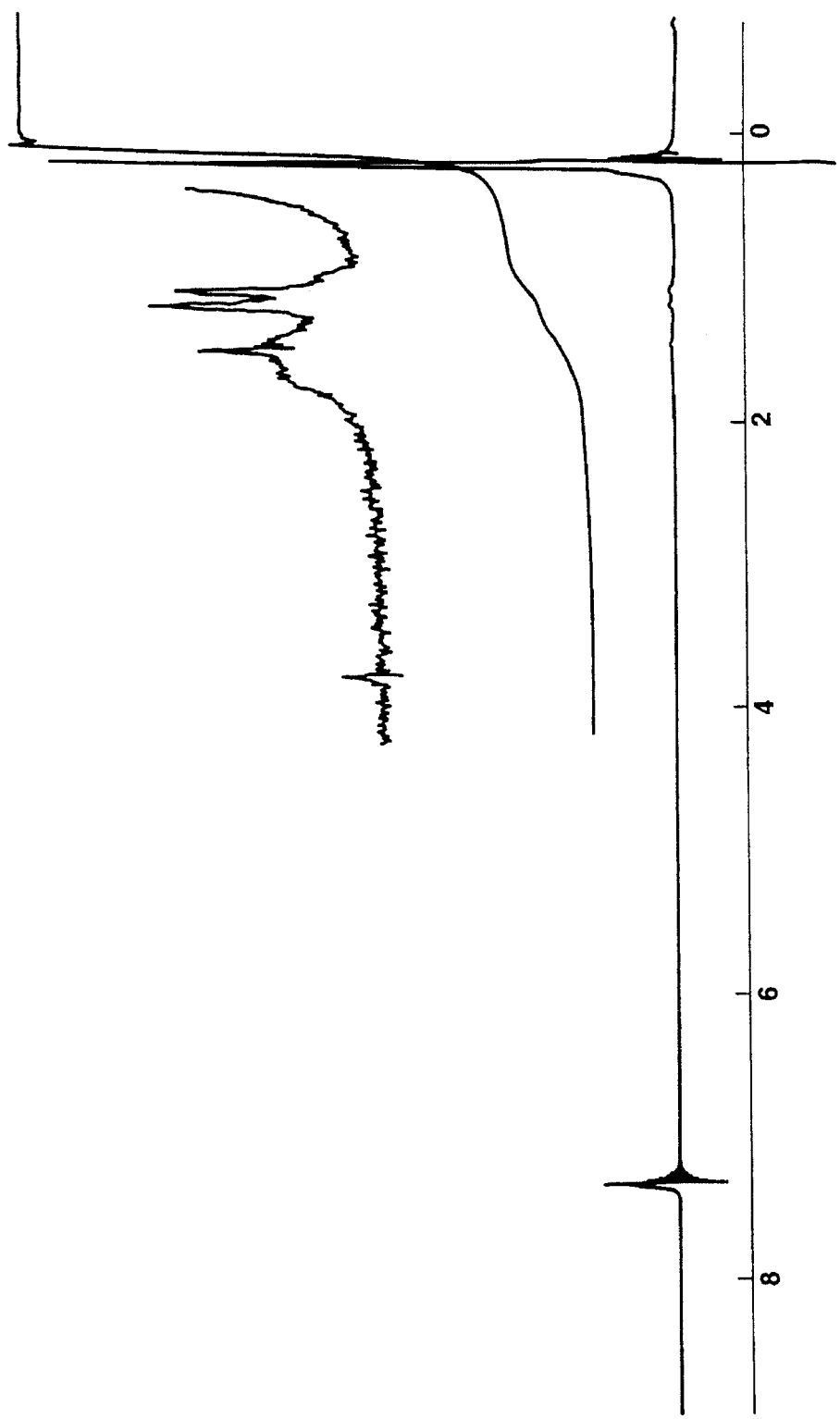
FIGS. 23 and 24 are $^1$H-NMR and IR spectra of the stannosiloxane of Example 12.
Figure 24:
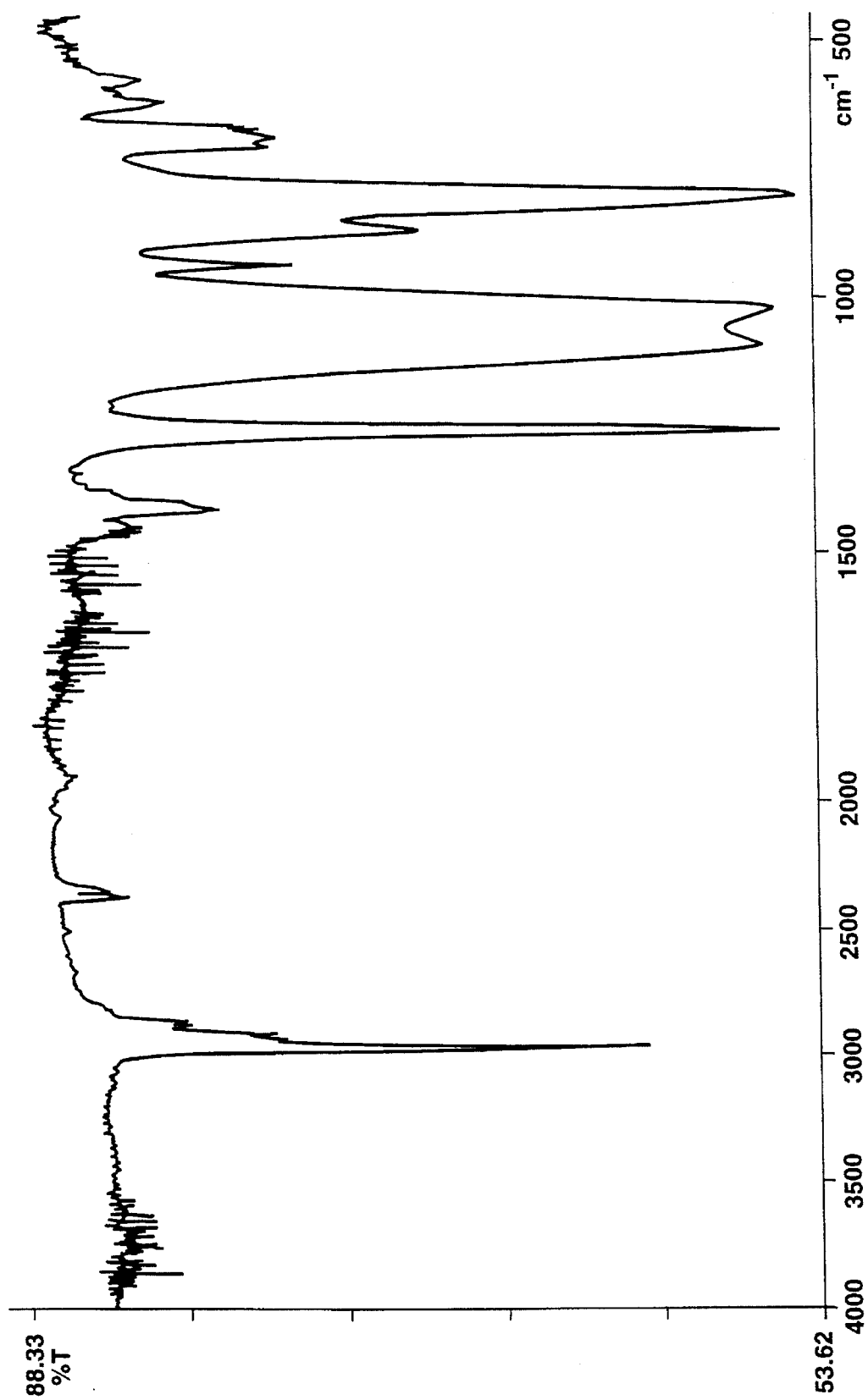

A 1-liter four-necked flask equipped with a stirrer, condenser, thermometer, and dropping funnel was charged with 213 grams of hexamethylcyclotrisiloxane, which was heated to 80° C. in a nitrogen atmosphere. To the flask, 35.4 grams of dibutyltin dimethoxide was added dropwise. The contents were stirred at 80° C. for 4 hours. After the disappearance of hexamethylcyclotrisiloxane was acknowledged by gas chromatography, the flask was cooled to room temperature. A mixture of water and methanol (22 grams/22 grams) was added to the reaction solution, which was stirred for 2 hours at room temperature. To the reaction solution was added 500 ml of toluene. The residual water was azeotroped off and the volatiles were distilled off at 120° C. and 4 mmHg. The product (220 grams) was a raw rubber like semi-solid. On analysis of $^1$H-NMR spectrum (FIG. 23) and IR spectrum (FIG. 24), it was identified to be a polystannosiloxane represented by the following average compositional formula. It had a polystyrene conversion number average molecular weight of 4,200.

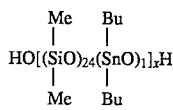

Example 13

Figure 25:
FIGS. 25 and 26 are $^1$H-NMR and IR spectra of the stannosiloxane of Example 13.
Figure 26:
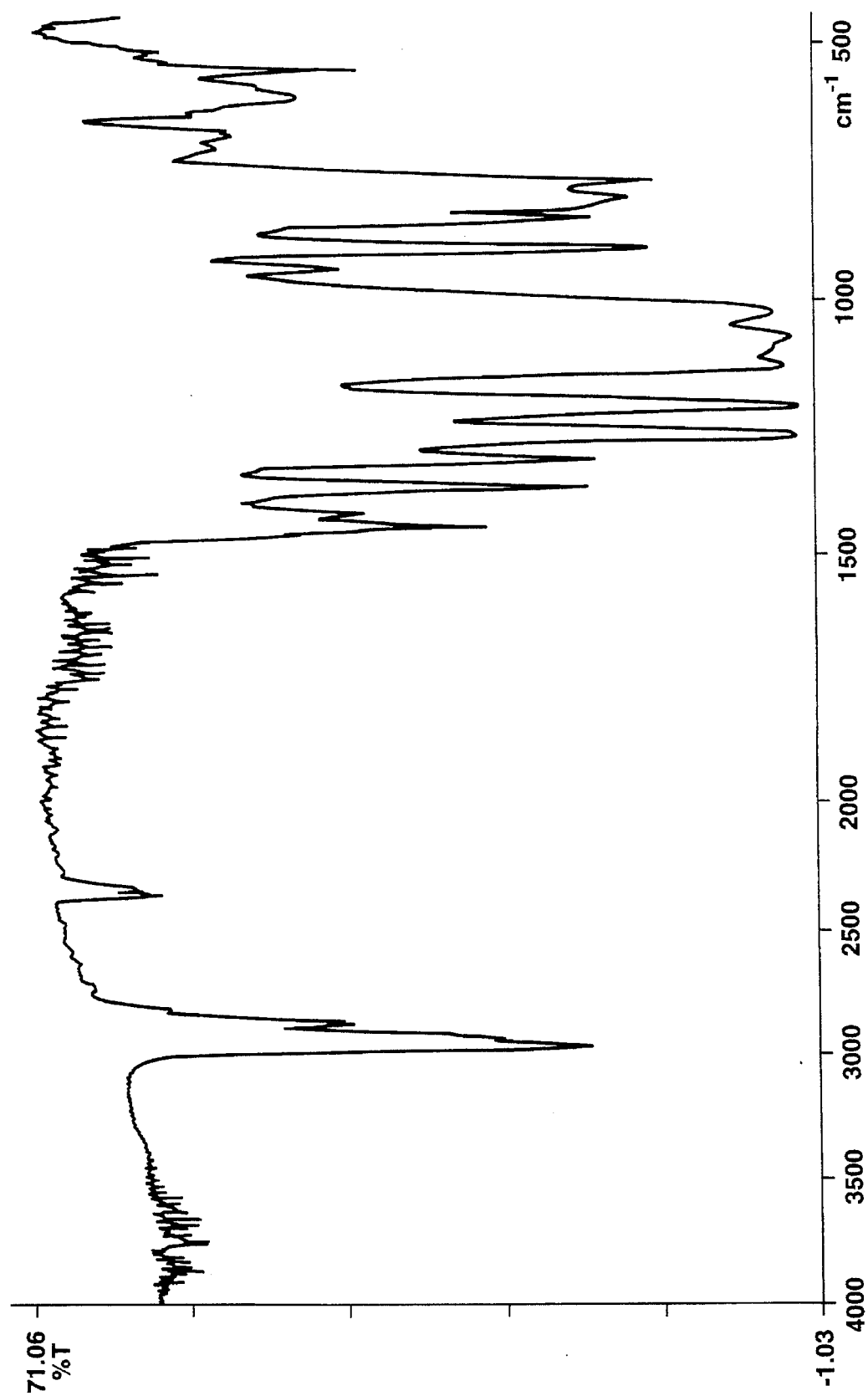

A 100-ml four-necked flask equipped with a stirrer, condenser, thermometer, and dropping funnel was charged with 65.6 grams of 1,3,5-tri(3,3,3-trifluoropropyl)-1,3,5-trimethylcyclotrisiloxane, which was heated to 80° C. in a nitrogen atmosphere. To the flask, 20.7 grams of dibutyltin dimethoxide was added dropwise. The contents were stirred at 80° C. for 4 hours. After the disappearance of 1,3,5-tri(3,3,3-trifluoropropyl)-1,3,5-trimethylcyclotrisiloxane was acknowledged by gas chromatography, the volatiles were distilled off at 120° C. and 4 mmHg. The product (78.2 grams) was a liquid having a viscosity of 380 centipoise. On analysis of $^1$H-NMR spectrum (FIG. 25) and IR spectrum (FIG. 26), it was identified to be a stannosiloxane represented by the following average compositional formula.

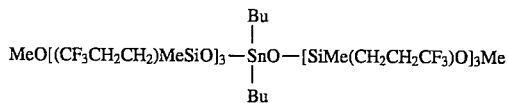

Example 14

Figure 27:
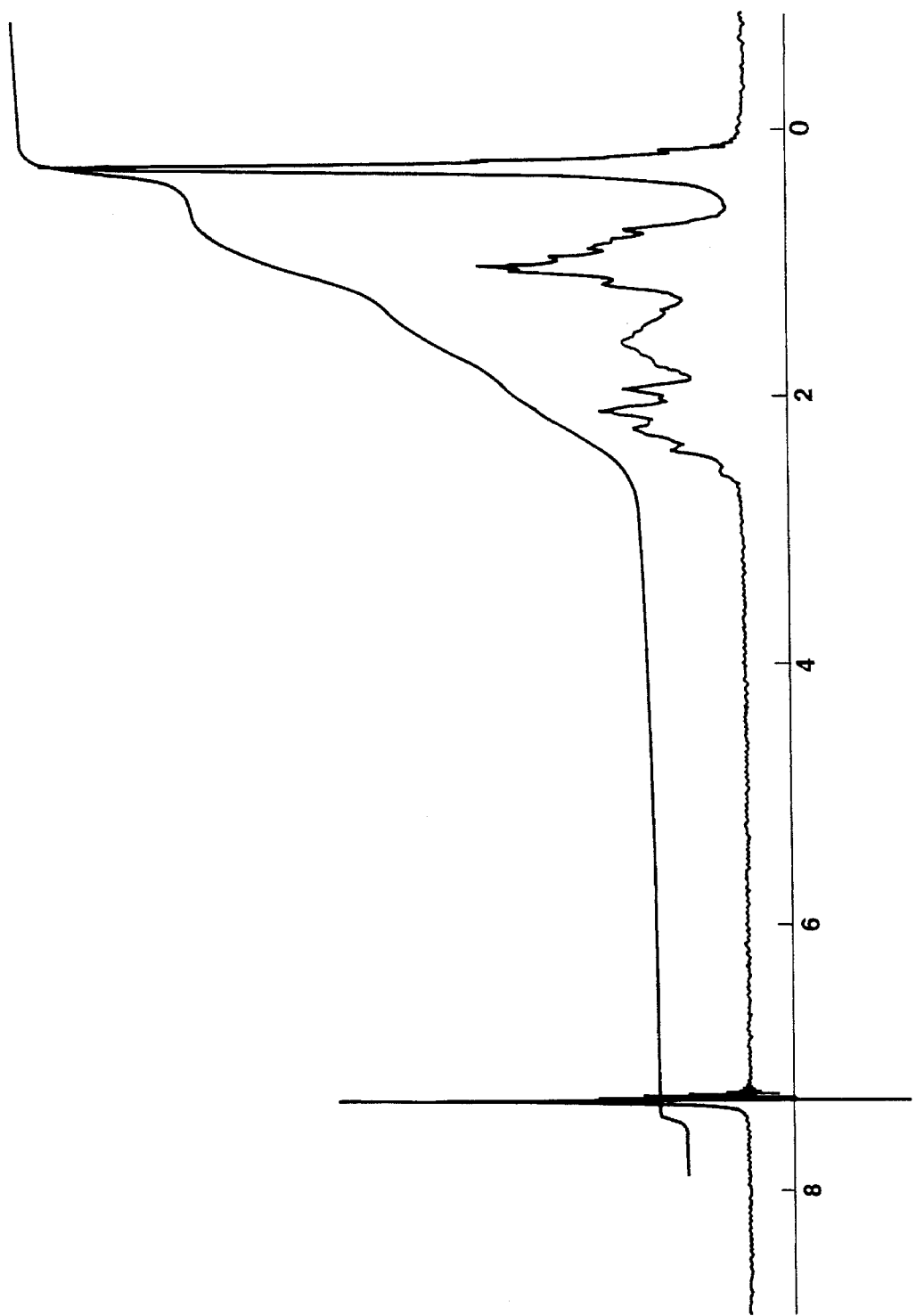
FIGS. 27 and 28 are $^1$H-NMR and IR spectra of the stannosiloxane of Example 14.
Figure 28:
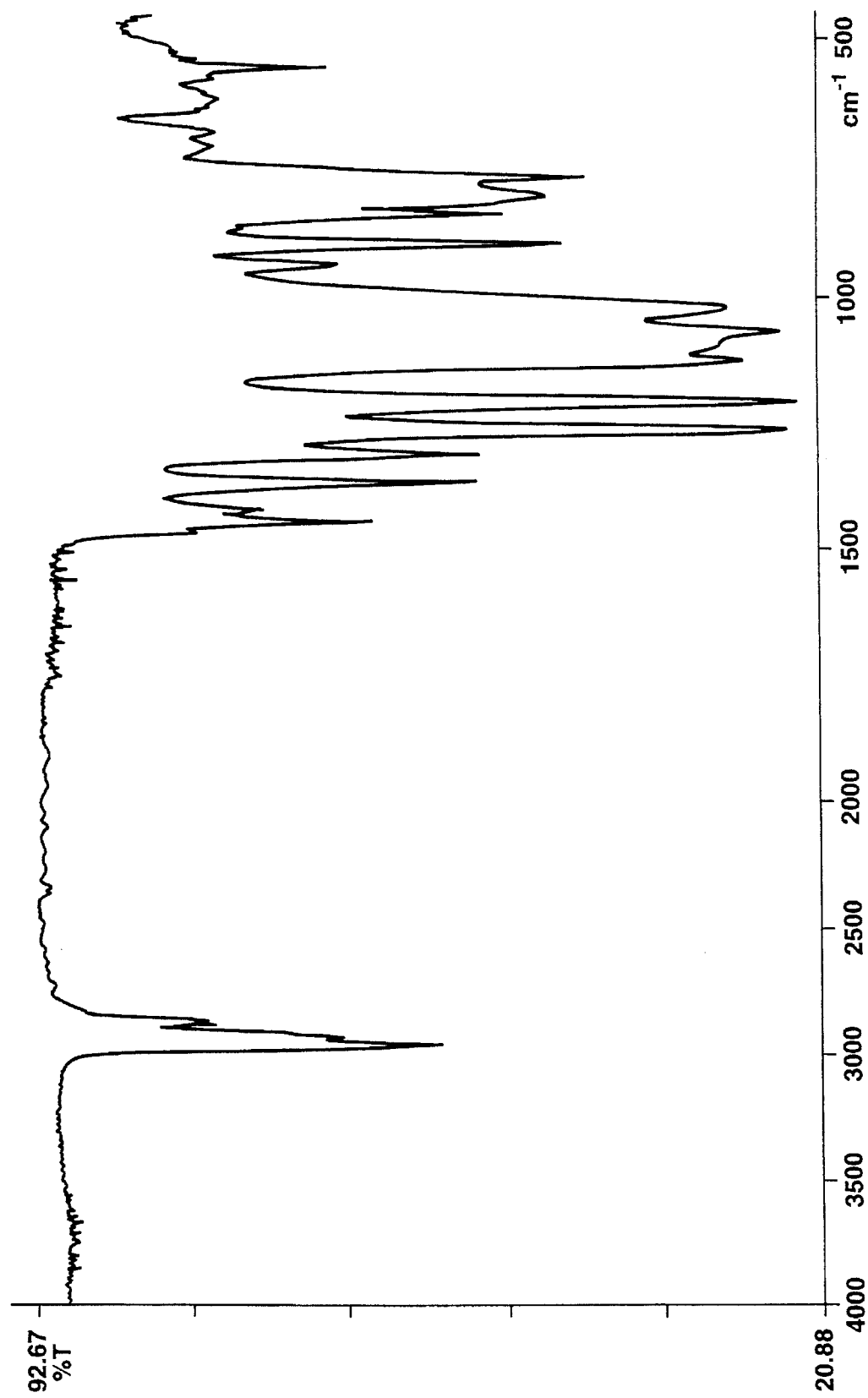

A 100-ml four-necked flask equipped with a stirrer, condenser, thermometer, and dropping funnel was charged with 141 grams of 1,3,5-tri(3,3,3-trifluoropropyl)-1,3,5-trimethylcyclotrisiloxane, which was heated to 80° C. in a nitrogen atmosphere. To the flask, 44.3 grams of dibutyltin dimethoxide was added dropwise. The contents were stirred at 80° C. for 4 hours. After the disappearance of 1,3,5-tri(3,3,3-trifluoropropyl)-1,3,5-trimethylcyclotrisiloxane was acknowledged by gas chromatography, a mixture of water and methanol (27 grams/27 grams) was added to the reaction solution, which was stirred for 2 hours at room temperature. The volatiles were distilled off at 120° C. and 4 mmHg. The product (176 grams) was a raw rubber-like semi-solid. On analysis of $^1$H-NMR spectrum (FIG. 27) and IR spectrum (FIG. 28), it was identified to be a polystannosiloxane represented by the following average compositional formula.

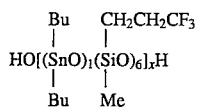

Japanese Patent Application Nos. 155139/1995, 155140/1995, and 183492/1995 are incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. An aluminosiloxane having at least one Al—O—Si linkage in its molecule and represented by the following general formula (1):

wherein R is a hydrogen atom or a substituted or unsubstituted monovalent hydrocarbon group having 1 to 20 carbon atoms, R' is a substituted or unsubstituted monovalent hydrocarbon group having 1 to 10 carbon atoms, letters k, m, and n are positive integers inclusive of 0, and k+m+n≧1.

2. A method for preparing an aluminosiloxane represented by the following general formula (1) of claim 1:

wherein R is a hydrogen atom or a substituted or unsubstituted monovalent hydrocarbon group having 1 to 20 carbon atoms, R' is a substituted or unsubstituted monovalent hydrocarbon group having 1 to 10 carbon atoms, letters k, m, and n are positive integers inclusive of 0, and k+m+n≧1, said method comprising the step of reacting an aluminum alkoxide of the following general formula (2):

$$Al(OR')_3 \qquad (2)$$

wherein R' is as defined above with a cyclotrisiloxane of the following general formula (3):

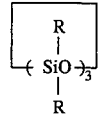

wherein R is as defined above.

3. A titanosiloxane having at least one Ti—O—Si linkage in its molecule and represented by the following general formula (4):

$$R'O(R_2SiO)_{3a}-Ti \begin{matrix} (OSiR_2)_{3b}OR' \\ -(OSiR_2)_{3c}OR' \\ (OSiR_2)_{3d}OR' \end{matrix} \qquad (4)$$

wherein R is a hydrogen atom or a substituted or unsubstituted monovalent hydrocarbon group having 1 to 20 carbon atoms, R' is a substituted or unsubstituted monovalent hydrocarbon group having 1 to 10 carbon atoms, letters a, b, c, and d are positive integers inclusive of 0, and $a+b+c+d \geq 1$.

4. A method for preparing a titanosiloxane represented by the following general formula (4) of claim 3:

$$R'O(R_2SiO)_{3a}-Ti \begin{matrix} (OSiR_2)_{3b}OR' \\ -(OSiR_2)_{3c}OR' \\ (OSiR_2)_{3d}OR' \end{matrix} \qquad (4)$$

wherein R is a hydrogen atom or a substituted or unsubstituted monovalent hydrocarbon group having 1 to 20 carbon atoms, R' is a substituted or unsubstituted monovalent hydrocarbon group having 1 to 10 carbon atoms, letters a, b, c, and d are positive integers inclusive of 0, and $a+b+c+d \geq 1$, said method comprising the step of reacting a titanium alkoxide of the following general formula (5):

$$Ti(OR')_4 \qquad (5)$$

wherein R' is as defined above with a cyclotrisiloxane of the following general formula (3):

$$\left[ \begin{matrix} R \\ | \\ SiO \\ | \\ R \end{matrix} \right]_3 \qquad (3)$$

wherein R is as defined above.

5. A stannosiloxane of the following general formula (6):

$$R^1O-(SiO)_{3x}-SnO-(SiO)_{3y}-R^1 \qquad (6)$$
with $R^3$ and $R^2$ and $R^3$ substituents wherein $R^1$ and $R^2$ are independently selected from substituted or unsubstituted monovalent hydrocarbon groups having 1 to 20 carbon atoms, $R^3$ is independently a hydrogen atom or substituted or unsubstituted monovalent hydrocarbon group having 1 to 10 carbon atoms, letters x and y are positive integers inclusive of 0 with the proviso that both x and y are not equal to 0 at the same time.

6. A polystannosiloxane of the following general formula (7):

$$R^4O-[(SiO)_{3x}-SnO-(SiO)_{3y}]_z-R^4 \qquad (7)$$
with $R^3$ and $R^2$ and $R^3$ substituents wherein $R^2$ is a substituted or unsubstituted monovalent hydrocarbon group having 1 to 20 carbon atoms, $R^3$ is a hydrogen atom or substituted or unsubstituted monovalent hydrocarbon group having 1 to 10 carbon atoms, $R^4$ is a hydrogen atom or substituted or unsubstituted monovalent hydrocarbon groups having 1 to 20 carbon atoms, letters x and y are positive integers inclusive of 0 with the proviso that both x and y are not equal to 0 at the same time, and z is an integer of at least 2.

7. A method for preparing a stannosiloxane of the following general formula (6) of claim 5:

$$R^1O-(SiO)_{3x}-SnO-(SiO)_{3y}-R^1 \qquad (6)$$
with $R^3$ and $R^2$ and $R^3$ substituents wherein $R^1$ and $R^2$ are independently selected from substituted or unsubstituted monovalent hydrocarbon groups having 1 to 20 carbon atoms, $R^3$ is independently a hydrogen atom or substituted or unsubstituted monovalent hydrocarbon group having 1 to 10 carbon atoms, letters x and y are positive integers inclusive of 0 with the proviso that both x and y are not equal to 0 at the same time, said method comprising the step of reacting a tin compound of the following general formula (8):

$$R^2{}_2Sn(OR^1)_2 \qquad (8)$$

wherein $R^1$ and $R^2$ are as defined above with a cyclotrisiloxane of the following general formula (9):

$$(R^3{}_2SiO)_3 \qquad (9)$$

wherein $R^3$ is as defined above.

8. A method for preparing a polystannosiloxane of the following general formula (7) of claim 6:

$$R^4O-[(SiO)_{3x}-SnO-(SiO)_{3y}]_z-R^4 \qquad (7)$$
with $R^3$ and $R^2$ and $R^3$ substituents wherein $R^2$ is a substituted or unsubstituted monovalent hydrocarbon group having 1 to 20 carbon atoms, $R^3$ is a hydrogen atom or substituted or unsubstituted monovalent hydrocarbon group having 1 to 10 carbon atoms, $R^4$ is a hydrogen atom or substituted or unsubstituted monovalent hydrocarbon groups having 1 to 20 carbon atoms, letters x and y are positive integers inclusive of 0 with the proviso that both x and y are not equal to 0 at the same time, and z is an integer of at least 2, said method comprising the step of subjecting to hydrolysis and polycondensation a stannosiloxane of the following general formula (6):

$$R^1O-(SiO)_{3x}-SnO-(SiO)_{3y}-R^1 \qquad (6)$$
with $R^3$ and $R^2$ and $R^3$ substituents wherein $R^1$ is a substituted or unsubstituted monovalent hydrocarbon group having 1 to 20 carbon atoms, and $R^2$, $R^3$, x and y are as defined above.

9. The aluminosiloxane of claim 1, wherein the R groups are, independently, an alkyl, cycloalkyl, phenyl, tolyl or alkenyl group of 1–20 carbon atoms optionally substituted by cyano groups, alkoxy groups or halogen atoms; the R' groups are, independently, an alkyl, cycloalkyl, phenyl or tolyl group of 1–10 carbon atoms optionally substituted by cyano groups, alkoxy groups or halogen atoms; k, m and n are from 0 to 5 and $k+m+n=1-15$.

10. The method of claim 2, wherein the R groups are, independently, an alkyl, cycloalkyl, phenyl, tolyl or alkenyl group of 1–20 carbon atoms optionally substituted by cyano groups, alkoxy groups or halogen atoms; the R' groups are, independently, an alkyl, cycloalkyl, phenyl or tolyl group of 1–10 carbon atoms optionally substituted by cyano groups, alkoxy groups or halogen atoms; k, m and n are from 0 to 5 and k+m+n=1–15.

11. The method of claim 2, wherein the molar ratio of aluminum alkoxide to cyclotrisiloxane is from 3/1 to 45/1.

12. The titanosiloxane of claim 3, w3herein the R groups are, independently, an alkyl, cycloalkyl, phenyl, tolyl or alkenyl group of 1–20 carbon atoms optionally substituted cyano groups, alkoxy groups or halogen atoms; the R' groups are, independently, an alkyl, cycloalkyl, phenyl or tolyl group of 1–10 carbon atoms optionally substituted by cyano groups, alkoxy groups or halogen atoms; a, b, c and d are from 0 to 5 and a+b+c+d=1–20.

13. The method of claim 4, wherein the R groups are, independently, an alkyl cycloalkyl, phenyl, tolyl or alkenyl group of 1–20 carbon atoms optionally substituted by cyano groups, alkoxy groups or halogen atoms; the R' groups are, independently, an alkyl, cycloalkyl, phenyl or tolyl group of 1–10 carbon atoms optionally substituted by cyano groups, alkoxy groups or halogen atoms; a, b, c and d are from 0 to 5 and a+b+c+d=1–20.

14. The method of claim 4, wherein the molar ratio of titanium alkoxide to cyclotrisiloxane is from 3/1 to 60/1.

15. The stannosiloxane of claim 5, wherein the $R^1$ and $R^2$ groups are, independently, an alkyl, cycloalkyl, phenyl, tolyl or alkenyl group of 1–20 carbon atoms optionally substituted by cyano groups, alkoxy groups or halogen atoms; the $R^3$ groups are, independently, an alkyl, cycloalkyl, phenyl, tolyl or alkenyl group of 1–10 carbon atoms optionally substituted by cyano groups, alkoxy groups or halogen atoms; and, $1 \leq x+y \leq 33$.

16. The method of claim 7, wherein the $R^1$ and $R^2$ groups are, independently, an alkyl, cycloalkyl, phenyl, tolyl or alkenyl group of 1–20 carbon atoms optionally substituted by cyano groups, alkoxy groups or halogen atoms; the $R^3$ groups are, independently, an alkyl, cycloalkyl, phenyl, tolyl or alkenyl group of 1–10 carbon atoms optionally substituted by cyano groups, alkoxy groups or halogen atoms; and, $1 \leq x+y \leq 33$.

17. The polystannosiloxane of claim 6, wherein the $R^2$ groups are, independently, an alkyl, cycloalkyl, phenyl, tolyl or alkenyl group of 1–20 carbon atoms optionally substituted by cyano groups, alkoxy groups or halogen atoms; the $R^3$ groups are, independently, an alkyl, cycloalkyl, phenyl, tolyl or alkenyl group of 1–10 carbon atoms optionally substituted by cyano groups, alkoxy group or halogen atoms; the $R^4$ groups are, independently, hydrogen or an alkyl, cycloalkyl, phenyl, tolyl or alkenyl group of 1–20 carbon atoms optionally substituted by cyano groups, alkoxy groups or halogen atoms; $1 \leq x+y \leq 33$; and, $z=2-1000$.

18. The method of claim 8, wherein the $R^2$ groups are, independently, an alkyl, cycloalkyl, phenyl, tolyl or alkenyl group of 1–20 carbon atoms optionally substituted by cyano groups, alkoxy groups or halogen atoms; the $R^3$ groups are, independently, an alkyl, cycloalkyl, phenyl, tolyl or alkenyl group of 1–10 carbon atoms optionally substituted by cyano groups, alkoxy groups or halogen atoms; the $R^4$ groups are, independently, hydrogen or an alkyl, cycloalkyl, phenyl, tolyl or alkenyl group of 1–20 carbon atoms optionally substituted by cyano groups, alkoxy groups or halogen atoms; $1 \leq x+y \leq 33$; and, $z=2-1000$.

\* \* \* \* \*